US011650338B2

(12) United States Patent
Kent

(10) Patent No.: US 11,650,338 B2
(45) Date of Patent: May 16, 2023

(54) SCINTILLATION DETECTOR

(71) Applicant: BAE SYSTEMS plc, London (GB)

(72) Inventor: Lionel William John Kent, Chelmsford Essex (GB)

(73) Assignee: BAE SYSTEMS PLC, London (GB)

( * ) Notice: Subject to any disclaimer, the term of this patent is extended or adjusted under 35 U.S.C. 154(b) by 0 days.

(21) Appl. No.: 17/292,625

(22) PCT Filed: Nov. 20, 2019

(86) PCT No.: PCT/GB2019/053288
§ 371 (c)(1),
(2) Date: May 10, 2021

(87) PCT Pub. No.: WO2020/104800
PCT Pub. Date: May 28, 2020

(65) Prior Publication Data
US 2022/0003883 A1 Jan. 6, 2022

(30) Foreign Application Priority Data

Nov. 23, 2018 (GB) ..................................... 1819119
Nov. 26, 2018 (GB) ..................................... 1819183
Jan. 29, 2019 (EP) ..................................... 19154080

(51) Int. Cl.
*G01T 1/208* (2006.01)
*G01T 1/20* (2006.01)
(Continued)

(52) U.S. Cl.
CPC ............ *G01T 1/208* (2013.01); *G01N 23/203* (2013.01); *G01T 1/20185* (2020.05); *G01T 1/40* (2013.01);
(Continued)

(58) Field of Classification Search
CPC ....... G01T 1/208; G01T 1/20185; G01T 1/40; G01N 23/203; G01N 2223/505; G01N 2223/639; A61B 6/4258
See application file for complete search history.

(56) References Cited

U.S. PATENT DOCUMENTS 3,790,785 A 2/1974 Paolini et al.
4,450,354 A 5/1984 Smith, Jr. et al.
(Continued)

FOREIGN PATENT DOCUMENTS

EP 0416970 A2 3/1991
GB 1560408 A 2/1980
(Continued)

OTHER PUBLICATIONS

International Preliminary Report on Patentability received for PCT Application No. PCT/GB2019/053288. dated Jun. 3, 2021. 7 pages.
(Continued)

*Primary Examiner* — Kiho Kim
(74) *Attorney, Agent, or Firm* — Finch & Maloney PLLC

(57) ABSTRACT

The scintillation detector assembly 10 comprises a first scintillation detector 11A of a set SSD of scintillation detectors 11, comprising a first scintillator 12A of a set SS of scintillators 12 and a first light sensor 13A of a set SLS of respective light sensors 13 optically coupled thereto, arranged to detect electromagnetic radiation and output a first signal; a first radiation source 14A of a set SRS of radiation sources 14, configured to emit first gamma radiation G1 of a first set SG of gamma radiation G, having a first reference energy RE1 of a set SRE of respective first reference energies RE; and a controller 15 configured to control a gain of the first scintillation detector 11A based, at
(Continued)

least in part, on the first gamma radiation, having the first reference energy, detected by the first scintillation detector 11A.

18 Claims, 12 Drawing Sheets

(51) Int. Cl.
  *G01N 23/203* (2006.01)
  *G01T 1/40* (2006.01)
  *A61B 6/00* (2006.01)
(52) U.S. Cl.
  CPC ...... *A61B 6/4258* (2013.01); *G01N 2223/505* (2013.01); *G01N 2223/639* (2013.01)

(56) References Cited

U.S. PATENT DOCUMENTS

| | | | |
|---|---|---|---|
| 4,580,048 A | | 4/1986 | Dion |
| 5,068,883 A | | 11/1991 | DeHaan et al. |
| 5,077,478 A | | 12/1991 | Walford |
| 2005/0263680 A1 | * | 12/2005 | Stein ............... H05B 45/12 250/238 |
| 2010/0168947 A1 | * | 7/2010 | Winso ............... G01T 1/20 250/363.01 |
| 2012/0201356 A1 | | 8/2012 | Rothschild et al. |
| 2016/0146948 A1 | | 5/2016 | Hovgaard |
| 2017/0336526 A1 | | 11/2017 | Arodzero et al. |
| 2019/0010611 A1 | | 1/2019 | Wilds et al. |

FOREIGN PATENT DOCUMENTS

| | | | | |
|---|---|---|---|---|
| GB | 2083618 A | | 3/1982 | |
| GB | 2463707 A | | 3/2010 | |
| GB | 2504771 A | * | 2/2014 | ............ G01T 1/362 |
| JP | 2004170122 A | * | 6/2004 | |
| WO | 8906357 | | 7/1989 | |
| WO | 9427138 A1 | | 11/1994 | |
| WO | 2012130335 A1 | | 10/2012 | |
| WO | 2012142453 A2 | | 10/2012 | |
| WO | 2019158902 A1 | | 8/2019 | |
| WO | 2020104800 A1 | | 5/2020 | |

OTHER PUBLICATIONS

International Search Report and Written Opinion received for PCT Application No. PCT/GB2019/053288. dated Feb. 17, 2020. 8 pages.
Search Report under Section 17(5) received for GB Application No. 1819119.7 dated May 31, 2019. 5 pages.
Search Report under Section 17(5) received for GB Application No. 1819183.3 dated May 31, 2019. 5 pages.
Extended European Search Report received for EP Application No. 19154080.6 dated Aug. 5, 2019. 7 pages.
International Preliminary Report on Patentability received for PCT Application No. PCT/GB2019/050312. dated Aug. 27, 2020. 8 pages.
International Search Report and Written Opinion received for PCT Application No. PCT/GB2019/050312. dated May 7, 2019. 12 pages.
GB Search Report under Section 17(5) received for GB Application No. 1802483.6, dated Aug. 14, 2018. 3 pages.
Extended European Search Report received for EP Application No. 18157006.0, dated Jul. 19, 2018. 9 pages.
GB Examination Report under Section 18(3) received for GB Application No. 1819183.3, dated Jun. 13, 2022. 3 pages.

* cited by examiner

SCINTILLATION DETECTOR

FIELD

The present invention relates to scintillation detectors, for example for detecting ionizing radiation, such as in Compton radiation backscatter detectors.

BACKGROUND TO THE INVENTION

Generally, scintillation detectors are used to detect ionizing radiation. Typically, a scintillation detector (also known as a scintillation counter) comprises a scintillator (also known as a scintillator material) and a light sensor. The scintillator exhibits scintillation (i.e. a property of luminescence), thereby emitting light when excited by the ionizing radiation. The light sensor absorbs the emitted light and generates an electrical output signal, typically via an output circuit. Scintillation detectors may be used in radiation detectors, for example Compton radiation backscatter detectors—which for example can be used to detect concealed materials.

However, energy responses of scintillators may drift, for example with temperature, thereby affecting the detection of an ionizing radiation spectrum. There are a number of techniques for dealing with this issue of thermal drift including, for example, placing temperature monitors around the scintillator to measure its temperature, and then using the temperature reading to adjust for example a 'Fine Gain' digital correction in the digitised output from the light sensor. These temperature monitors only provide localised temperature measurements of the scintillator, which is a problem when environmental temperatures are changing. Additionally the gain of the electrical circuit measuring the charge pulse produced by a radiation detection event may also drift. A number of solutions for this issue including the placement of a calibrated light source such as an LED on the scintillator that produces a well-defined pulse of light within the scintillator. This then be used to calibrate the charge pulse produced by a known optical input.

Hence, there is a need to improve scintillation detectors.

SUMMARY OF THE INVENTION

It is one aim of the present invention, amongst others, to provide a scintillation detector assembly which at least partially obviates or mitigates at least some of the disadvantages of the prior art, whether identified herein or elsewhere. For instance, it is an aim of embodiments of the invention to provide a scintillation detector assembly that more accurately, precisely and/or reproducibly detects ionizing radiation, particularly a spectrum and/or an energy value thereof.

A first aspect provides a scintillation detector assembly comprising:

a first scintillation detector of a set of scintillation detectors, comprising a first scintillator of a set of scintillators and a first light sensor of a set of respective light sensors optically coupled thereto, arranged to detect electromagnetic radiation and output a first signal;

a first radiation source of a set of radiation sources, configured to emit first gamma radiation of a first set of gamma radiation, having a first reference energy of a set of respective first reference energies; and a controller configured to control a gain of the first scintillation detector based, at least in part, on the first gamma radiation, having the first reference energy, detected by the first scintillation detector.

A second aspect provides a Compton radiation backscatter detector comprising a scintillation detector assembly according to the first aspect.

A third aspect provides a method of controlling a scintillation detector assembly comprising a first scintillation detector of a set of scintillation detectors, comprising a first scintillator of a set of scintillators and a first light sensor of a set of respective light sensors optically coupled thereto, arranged to detect electromagnetic radiation, the method comprising:

detecting, by the first scintillation detector, first gamma radiation of a first set of gamma radiation, having a first reference energy of a set of first respective reference energies; and controlling a gain of the first scintillation detector based, at least in part, on the first gamma radiation, having the first reference energy, detected by the first scintillation detector.

A fourth aspect provides a method of detecting a target using a scintillation detector assembly, the method comprising:

acquiring a background Compton backscatter spectrum and a Compton backscatter spectrum of the target; and background-subtracting from the Compton backscatter spectrum of the target using the background Compton backscatter spectrum;

wherein the scintillation detector assembly is controlled according to the method the third aspect.

A fifth aspect provides use of gamma radiation, having a reference energy, to control gain of a scintillation detector comprising a scintillator and a light sensor optically coupled thereto.

A sixth aspect provides a tangible non-transient computer-readable storage medium having recorded thereon instructions which when implemented by a computer device comprising a processor and a memory, cause the computer device to perform a method according to the third aspect or the fourth aspect.

DETAILED DESCRIPTION OF THE INVENTION

According to the present invention there is provided a scintillation detector assembly, as set forth in the appended claims. Also provided are a Compton radiation backscatter detector comprising a scintillation detector assembly, a method of controlling a scintillation detector assembly, a method of detecting a target using a scintillation detector assembly and use of gamma radiation, having a reference energy, to control gain of a scintillation detector. Other features of the invention will be apparent from the dependent claims, and the description that follows.

Scintillation Detector Assembly

The first aspect provides a scintillation detector assembly comprising:

a first scintillation detector of a set of scintillation detectors, comprising a first scintillator of a set of scintillators and a first light sensor of a set of respective light sensors optically coupled thereto, arranged to detect electromagnetic radiation and output a first signal;

a first radiation source of a set of radiation sources, configured to emit first gamma radiation of a first set of gamma radiation, having a first reference energy of a set of respective first reference energies; and a controller configured to control a gain of the first scintillation detector based, at least in part, on the first gamma radiation, having the first reference energy, detected by the first scintillation detector.

In this way, the gain of the first scintillation detector may be controlled to compensate for drift, for example due to changes in temperature of the first scintillator. Additionally and/or alternatively, the gain of the first scintillation detector may be controlled to compensate for drift, for example in a gain of the first light sensor, such as a photomultiplier, and/or in an absolute accuracy of a charge measurement circuit configured to output the first signal. Particularly, the first reference energy is used as a reference and the gain of the first scintillation detector controlled to maintain the first reference energy, as determined from the first signal, invariant and/or quasi invariant (i.e. constant, not changing, not drifting). In contrast with the conventional techniques for dealing with the issue of thermal drift including, for example using temperature monitors (i.e. indirect compensation), use of the first reference energy of the first gamma radiation as the reference for controlling the gain provides direct compensation for drift of the first scintillation detector, since the first gamma radiation is detected in a same way as ionizing radiation of interest, for example of a target. Furthermore, in contrast with the conventional techniques for dealing with the issue of thermal drift, use of the first reference energy of the first gamma radiation as the reference for controlling the gain may compensate for drift, for example in the gain of the first light sensor, such as a photomultiplier, and/or in an absolute accuracy of a charge measurement circuit configured to output the first signal.

In more detail, when a gamma photon (or other ionizing radiation such as an alpha or beta particle) is absorbed by first scintillator, the first scintillator generates one or more luminescent photons in the visible range of the electromagnetic spectrum. The number of photons generated is directly proportional to the energy of the absorbed gamma photon. However, the number of luminescent photons (i.e. the number of photons in the visible range) generated by the first scintillator also varies as a function of the temperature thereof. Furthermore, the energy of the gamma photon is calculated from a charge pulse (i.e. the first signal) generated by the first light sensor, for example by a photomultiplier circuit, and measured as a charge. In other words, the first signal is measured, for example by integrating the charge pulse. In addition to the number of luminescent photons generated by the first scintillator varying as a function of the temperature thereof, a gain of the first light sensor, for example of the photomultiplier circuit, also appears to change time while changes in efficiency of the first scintillator (for example, due to radiation damage), such that there are two or more effects occur. That is, the first signal, for example the charge pulse, may be subject to changes in the luminescent pulse, changes in efficiency of the first scintillator and/or to variations in the gain of the first light sensor, for example of the photomultiplier circuit.

By way of example, consider a Compton radiation backscatter detector, such as used to detect for concealed targets such as explosives or narcotic compounds. Briefly, a target is exposed to gamma radiation and Compton radiation backscattered from the target is detected, for example by the first scintillation detector. The target may be identified from the backscattered Compton radiation, for example from a spectrum or features thereof.

In addition, some radiation emitted by the Ba-133 (particularly the 356 keV line i.e. the first reference energy) penetrates the lead shield in which the Ba-133 is housed and is detected directly by the first scintillation detector. For example, between 35.5% and 47.85 of the 346 keV line penetrates through 3.4 mm Pb (e.g. side wall of a source housing), while only between 11.9% and 21.9% of the 346 keV line penetrates through 7 mm Pb (e.g. base of a source housing). The transmission range values cited for each gamma energy above are a consequence of the fact that the gamma passing through the walls of the lead shield are subject to two separate energy loss mechanisms: Photoelectric absorption, and Compton Scattering. The photoelectric absorption process alone gives the maximum possible transmission values above, and in practice will be an significant overestimate since any Compton scattered gamma will be also be subject to significant absorption losses. The minimum transmission range values applies to the gamma that passes through the shield without incurring any inelastic scattering energy loss.

All charge generated by the first scintillation detector, including backscattered Compton radiation and the 356 keV line emitted by the Ba-133 that penetrates the lead shield, is channelised by a multichannel analyser. Hence, there is a direct mapping between the channel number and the response (i.e. the first signal) of the 356 keV line. This direct mapping is exploited to provide a system calibration (i.e. of the first scintillation detector). In effect, the gain of the system can be controlled so that the 356 keV line sits in or on a specific channel number. The energy of the gamma photon is directly proportional to the specific channel number (i.e. a peak response). Hence, by sitting the peak of the 356 keV line into the specific channel number by controlling the gain, the required calibration is obtained.

Particularly, a slope of the mapping between the multichannel analyser's channel number and the corresponding gamma energy has been found to vary linearly with the gamma energy. However this linear relationship does not necessarily have a constant fixed gradient that is independent of the scintillator temperature or other circuit drift effects. Since for example number of luminescence photons is a function of the scintillator temperature this gradient between channel number and energy will inevitably change with temperature. Hence, if the Compton radiation backscatter detector also uses Am-241 having a 59.54 keV line in combination with the 356 keV of Ba-133, then any variation of the slope of the mapping between channel numbers at respectively 59.54 keV and the 356 keV lines, due to effects like temperature, may be calibrated out. For example, an explosives detector based on the Compton radiation backscatter detector may include an Am-241 source shielded beside the first scintillator and be selectively exposed (for example via a lead shutter) for calibration using the 59.54 keV line—to illuminate with the 59.54 keV gamma emission line and then close. Then detect the desired backscatter spectrum where the 59.54 keV gamma of Am-241 yields backscatter around 48.3+ keV, the 81 keV emission line of Ba-133, and the 356 keV emission line of Ba-133 gives backscatter around 146.7+ keV. The 48.3+ keV backscatter is because Compton scattering angles of less than 180° will yield a smaller energy loss for the outgoing gamma. Since geometrically scattering at angles less than 180° is more probably to be detected, the backscatter peak will be at a higher energy. For example, backscatter peaks off a target may be observed at about ~50 keV for scattering of the 59.54 keV emission line. Meanwhile the 356 keV gamma emission line Ba-133 line that penetrates through the lead (or otherwise) shield of the source to the scintillator detector provides a continuous monitoring function such that drifts in the response of the first scintillation detector are identified and the gain thereof controlled thereby. Advantageously, an Am-241 radiation source emits no significant gamma radiation above 60 keV and since the 59.54 keV gamma radiation emitted by Am-241 can be effectively totally suppressed by a 2.5 mm thick Pb shield, the first scintillation detector may be selectively shielded from and exposed to the Am-241 radiation source, for example using a Pb shutter that provides a shield in a closed configuration and an exposing aperture in an open configuration. The Pb shield could be thinner: for example, a 1.5 mm thick Pb shield would reduce the transmission of the 59.54 keV line to less than 0.0607%. Total energy absorption in 1.5 mm of lead is 99.926%. Note some of the backscattered signal would depart via an entrance of the source housing and not be absorbed. By significant gamma radiation, it should be understood that the Gamma Transitions and Internal Conversion Coefficient tables ('LNE-LNHB/CEA-Table de Radionucléides', V. P. Chechev; N. K. Kuzmenko, pp 1-6; Oct. 20, 2000-; 241-Am-95) show that Am-241 does produce a whole series of gamma at much higher energies, but in all cases with a really small branching ratio probability. In any case, these very weak gamma would form part of the background/breakthrough spectrum, and so when subtracted from the target spectrum of interest would have no effect on the accuracy of the final corrected spectrum.

TABLE 1

180° Backscatter Energies for Various Gamma Emission Lines

| Line No | Radio-isotope Source | Energy of Gamma Emission Line (keV) | Energy Corresponding of 180° Backscattered Gamma (keV) |
|---|---|---|---|
| 1 | Am-241† | 26.3 | 23.84 |
| 2 | Ba-133 | 30.97 | 27.6 |
| 3 | Eu-152 | 40.11 | 34.7 |
| 4 | Ba-133 | 53.16 | 44.0 |
| 5 | Am-241 | 59.54 | 48.3 |
| 6 | Ba-133 | 80.99 | 61.5 |
| 7 | Eu-152 | 121.78 | 82.5 |
| 8 | Eu-152 | 244.69 | 125.0 |
| 9 | Ba-133 | 302.85 | 138.6 |
| 10 | Eu-152 | 344.27 | 146.7 |
| 11 | Ba-133 | 356.01 | 148.7 |

†Gamma emitted by the short lived metastable state of the Np237 nucleus that is formed when Am-241 decays by emitting an alpha particle.

Using the first reference energy (i.e. the 356 keV line in this example) provides for one point calibration, allowing for real-time (i.e. in situ) compensation of thermal drift, for example. A spectrum may be shifted along the channel number axis, for example positively or negatively. In this way, start-up of the first scintillation detector and hence of the Compton radiation backscatter detector may be accelerated, since thermal equilibration of the first scintillation detector may not be required. Furthermore, changes to the environment (such as ambient and/or operating temperature) and/or changes in efficiency (such as due to radiation damage) of the first scintillation detector may also be compensated for.

Additionally and/or alternatively to one point calibration, two or multi-point calibration may be provided, in which two or more different lines (i.e. of different energies) are detected. In this way, in addition to shifting the spectrum along the channel number axis, the spectrum may be expanded and/or contracted therealong, for example globally (two point calibration) or locally (multi-point calibration). By including the origin as a point, a single line may be used to provide two point calibration).

Additionally and/or alternatively, if an intensity of the first reference energy is substantially constant during analysis (or may be adjusted according to a half-life of the first radiation source, for example), semi-quantitative or even quantitative analysis may be performed, using the first reference energy as an internal standard, for example.

Additionally and/or alternatively, when measuring a Compton radiation backscatter spectrum, it is preferable to subtract a breakthrough spectrum, which is due to radiation from the sources penetrating directly through the source shields. By subtracting the breakthrough spectrum from the measured Compton radiation backscatter spectrum, a corrected Compton backscatter spectrum is obtained. However, such correction is conventionally not possible if the temperature has drifted between measuring the breakthrough spectrum and the Compton radiation backscatter spectrum, since a relative shift between the two spectra results in spectral artefacts, such as characteristic valleys having negative intensities. In contrast, by controlling the gain as described herein according to the first aspect, such correction by subtraction is enabled.

It should be understood that the scintillation detector assembly comprises the first scintillation detector, the first light sensor, the first radiation source and the controller.

In one example, the scintillation detector assembly comprises a circuit, for example a charge measurement circuit, electrically coupled to the first light sensor and configured to output the first signal. In one example, the first light sensor is electrically coupled to a channel analyser, for example a dual or a multi-channel analyser, for example via a charge pulse bus, configured to transmit a charge pulse associated with an absorbed photon to the analyser. In one example, the channel analyser is configured to collect, for example integrate or sum, all of charge pulses associated with a gamma absorption event and channelize the collected charge to yield a detected gamma energy value. For example, the Compton backscattered gamma may suffer a sequence of scattering events before eventually being absorbed completely by a photoelectric absorption event in the first scintillator. Each of these Compton scatter events would all happen so quickly that the effect will be as if the gamma photon had been absorbed in a single photoionisation event. In one example, the detected gamma energy value is digitised may be transmitted to a hub, for example, such as via a digital data bus that is associated with the particular channel, and hence to the controller (also known as a system controller, such as a computer), as described below in more detail.

At least some of the example embodiments described herein may be constructed, partially or wholly, using dedicated special-purpose hardware. Terms such as 'component', 'module', 'controller' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processor circuits. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The first scintillation detector is of the set of scintillation detectors. In one example, the set of scintillation detectors comprises M scintillation detectors, where M is a natural number greater than or equal to 1, for example 1, 2, 3, 4, 5, 6, 7, 8, 9, 10 or more. In one example, each scintillation detector of the set thereof may be as described with respect to the first scintillation detector. Conversely, in one example, one or more of the scintillation detectors may be different from the others of the set thereof, for example having scintillators of different materials and/or different light sensors, so as to detect radiation with different efficiencies. In one example, the scintillation detectors of the set thereof are arranged regularly, for example in an array.

The first scintillation detector is arranged to detect electromagnetic radiation, for example ionizing radiation such as gamma rays or photons, and output a first signal.

The first scintillation detector comprises the first scintillator of the set of scintillators. In one example, the set of scintillators comprises N scintillators, where N is a natural number greater than or equal to 1, for example 1, 2, 3, 4, 5, 6, 7, 8, 9, 10 or more. In one example, each scintillator of the set thereof may be as described with respect to the first scintillator. Conversely, in one example, one or more of the scintillators may be different from the others of the set thereof, for example being of different materials, so as to detect radiation with different efficiencies. In one example, the scintillators of the set thereof are arranged regularly, for example in an array.

In one example, the first scintillator comprises an inorganic crystal, for example NaI(Tl) (thallium-doped sodium iodide), CsI(Tl), CsI(Na), CsI(pure), CsF, KI(Tl), LiI(Eu), BaF2, CaF2(Eu), ZnS(Ag), CaWO4, CdWO4, YAG(Ce) (Y3Al5O12(Ce)), GSO, LSO, LaCl3(Ce), LaBr3(Ce), LYSO (Lu0.8Y0.2SiO5(Ce)) and/or BGO. Other scintillator materials are known.

The first scintillation detector comprises the first light sensor of the set of respective light sensors optically coupled to the set of scintillators. In one example, the set of respective light sensors comprises P light sensors, where P is a natural number greater than or equal to 1, for example 1, 2, 3, 4, 5, 6, 7, 8, 9, 10 or more. In one example, each light sensor of the set thereof may be as described with respect to the first light sensor. Conversely, in one example, one or more of the light sensors may be different from the others of the set thereof, for example being of different types, so as to detect light with different efficiencies. In one example, the light sensors of the set thereof are arranged regularly, for example in an array.

In one example, the first light sensor comprises a photomultiplier tube (PMT), photodiode, or silicon photomultiplier, for example an avalanche photodiode or a single photon avalanche photodiode (SPAD).

The scintillation detector assembly comprises the first radiation source of the set of the radiation sources, configured to emit the first gamma radiation of the first set of gamma radiation, having the first reference energy of the set of respective first reference energies. In one example, the set of radiation sources comprises Q radiation sources, where Q is a natural number greater than or equal to 1, for example 1, 2, 3, 4, 5, 6, 7, 8, 9, 10 or more. In one example, each radiation source of the set thereof may be as described with respect to the first radiation source. Conversely, in one example, one or more of the radiation sources may be different from the others of the set thereof, for example including different radio-nucleotides, so as to emit gamma radiation having different reference energies. In one example, the radiation sources of the set thereof are arranged regularly, for example in an array. In one example, the first set of gamma radiation comprises R gamma radiation (i.e. peaks, lines), where R is a natural number greater than or equal to 1, for example 1, 2, 3, 4, 5, 6, 7, 8, 9, 10 or more.

It should be understood that the R gamma radiation are mutually different i.e. having different respective energies. In one example, the set of respective first reference energies comprises S first reference energies, where S is a natural number greater than or equal to 1, for example 1, 2, 3, 4, 5, 6, 7, 8, 9, 10 or more. It should be understood that the S first reference energies are mutually different i.e. having different respective energies. One or more of the gamma radiation may be used as reference energies. That is, not all the gamma radiation may be useful, in practice, as reference energies, for example due to insufficient intensity and/or overlap with other peaks or lines.

In one example, the first radiation source comprises Ba-133, Am-241 and/or Eu-152. In one example, the set of radiation sources comprises Q radiation sources, including zero, one or more of each of Ba-133, Am-241 and/or Eu-152.

Am-241 sources emit both alpha particles and gamma radiation. Each Am-241 source may be 'sealed' to prevent unintentional release of radioactive material into the environment, and may have an activity of 29.6 kBq, for example as typical of domestic smoke detectors. The low energy gamma rays radiated by the Am-241 sources are mainly 59.54 keV, but there are also much weaker emissions at both 26.3 keV and 13.9 keV. The half-life of Am-241 is 432.2 years. In one example, the set of respective first reference energies, wherein the first radiation source comprises Am-241, comprises and/or consists of one or more of 13.9 keV, 26.3 keV and 59.54 keV.

Ba-133 sources emit both beta particles and gamma radiation. Each Ba-133 source may be 'sealed', and may have an activity of 100 kBq, for example. The stainless steel walls of the capsule of the GBa3.11 Ba-133 source design will stop within the capsule all beta particle emission by the Ba-133 radio isotope. Ba-133 emits both the low energy gamma rays which are used in the Compton Backscatter Spectroscopy measurements, and high energy gamma rays which are a significant health threat if the sources are handled directly. In the event of ingestion or inhalation, a 100 kBq Ba-133 source is much less harmful radiologically than a 29.6 kBq Am-241 source, being an alpha particle emitter also. The gamma rays emitted by the Ba-133 sources are as follows:

53.161 keV-2.14% BR;
79.621 keV-2.63% BR (Compton backscatter line overlapping with 80.9 keV line);
80.997 keV-33.31% BR (main Compton backscatter line of interest);
160.613 keV-0.638% BR (weak emission line);
223.398 keV-0.45% BR (weak emission line);
276.398 keV-7.13% BR;
302.853 keV-18.31% BR;
356.017 keV-62.05% BR;
383.851 keV-8.94% BR.

where BR is the Branching Ratio, the percentage of radioactive decays of Ba-133 that yield the associated gamma emission line. There are also two strong X-ray lines at 30.973 keV and 30.625 keV due to atomic transitions in the electronical excited Cs daughter atom formed by the decay of Ba-133. The higher energy emission lines of the Ba-133 source can be stopped with a relatively practical thickness of lead or tungsten shielding. For example 0.7 cm of Pb or 0.6 cm of W will reduce the received dose rate of the Ba-133 source at a given range by a factor of 10. Particularly, such Pb or W may effectively stop the 53.161 keV, 79.621 keV and/or 80.997 keV gamma emission lines of Ba-133. The half-life of Ba-133 is 10.51 years. In one example, the set of respective first reference energies, wherein the first radiation source comprises Ba-133, comprises and/or consists of one or more of 53.161 keV, 79.621 keV, 80.997 keV, 160.613 keV, 223.398 keV, 276.398 keV, 302.853 keV, 356.017 keV and 383.851 keV. Preferably, the first reference energy, wherein the first radiation source comprises Ba-133, is 356.017 keV (referred to herein as 356 keV).

Some information on the absorption by lead of these higher energy gamma of Ba-133. However the higher energy gamma emissions at 302.9 keV, 356 keV and 383.9 keV are all only partly stopped by the 3.4 mm thick side walls and 7 mm thick base of the lead shields. The transmissions of these gammas are:
- <33.2% and >24.3% of the 302.8 keV emission line through the shield's side wall.
- <10.4% and >5.5% of the 302.8 keV emission line through the shield's 7 mm thick base.
- <47.8% and >35.5% of the 356 keV emission line through the shield's side wall.
- <21.9% and >11.9% of the 356 keV emission line through the shield's 7 mm thick base.
- <54.4% and >40.8% of the 383.9 keV emission line through the shield's side wall.
- <28.7% and >15.8% of the 383.9 keV emission line through the shield's 7 mm thick base.

The transmission range values cited for each gamma energy above are a consequence of the fact that the gamma passing through the walls of the lead shield are subject to two separate energy loss mechanisms: Photoelectric absorption, and Compton Scattering. The photoelectric absorption process alone gives the maximum possible transmission values above, and in practice will be an significant overestimate since any Compton scattered gamma will be also be subject to significant absorption losses. The minimum transmission range values apply to the gamma that pass through the shield without incurring any inelastic scattering energy loss.

The single Eu-152 source used on the programme emits both beta particles and gamma radiation. The Eu-152 source is 'sealed', and has an activity of 100 kBq. The stainless steel walls of the capsule of the GEu2.11 Eu-152 source design will stop within the capsule all beta particle emission by the Eu-152 radio isotope. Eu-152 emits both a relatively low energy gamma ray at 121.78 keV which will be used in the Compton Backscatter Spectroscopy measurements, and 6 other high energy gamma lines which are a significant health threat if the sources are handled directly. The most significant in terms of the branching ratio of the gamma rays emitted by the Eu-152 sources are as follows:
- 121.78 keV-28.41% BR (main Compton backscatter line of interest);
- 244.69 keV-7.75% BR
- 344.28 keV-26.59% BR;
- 778.9 keV-12.97% BR;
- 964.08 keV-14.5% BR;
- 1085.83 keV-10.13% BR;
- 1112.07 keV-13.41% BR; and
- 1408.01 keV-20.85% BR;

where BR is the Branching Ratio, the percentage of radioactive decays of Eu-152 that yield the associated gamma emission line. There are also strong X-ray emission lines at 39.5229 keV, 40.1186 keV and weaker X-rays at 45.289 keV, 45.413 keV 45.731 keV, and finally some weaker still X-rays at 46.575 keV, 46.705 keV and 46.813 keV. These are all due to atomic transitions. These two closely spaced lines at 39.5229 and 40.1186 keV are clearly visible in the emission line spectra of FIGS. 13 and 14 used to create a channel to energy calibration mapping. In the right hand side of this spectral feature is a unresolved feature which is due to the other gamma listed above. The high energy gamma emission lines of the Eu-152 are difficult to stop, requiring for example 3.8 cm of lead or 2.5 cm of tungsten to reduce the received radiation dose rate by a factor of 10. The half-life of Eu-152 is 13.54 years. In one example, the set of respective first reference energies, wherein the first radiation source comprises Ba-133, comprises and/or consists of one or more of 121.78 keV, 344.28 keV, 778.9 keV, 964.08 keV, 1085.87 keV, 1112.07 keV and 1408.01 keV. Preferably, the first reference energy, wherein the first radiation source comprises Eu-152, is 121.7 keV. However, such energy is completely stopped by 7 mm of Pb, for example, so is more useful for unshielded (e.g. shuttered) or thinner shield applications.

In one example, the first radiation source is configured to emit second gamma radiation of the first set of gamma radiation, having a second reference energy of the set of respective first reference energies; and wherein the controller is configured to control the gain of the first scintillation detector based, at least in part, on the second gamma radiation of the first set of gamma radiation, having the second reference energy of the set of respective first reference energies, detected by the first scintillation detector.

That is, two different gamma lines from the first radiation source may be used to control the gain of the first scintillation detector, as described above.

In one example, the scintillation detector assembly comprises a second radiation source of the set of radiation sources, configured to emit first gamma radiation of a second set of gamma radiation, having a first reference energy of a set of respective second reference energies; and wherein the controller is configured to control the gain of the first scintillation detector based, at least in part, on the first gamma radiation of the second set of gamma radiation, having the first reference energy of the set of respective second reference energies, detected by the first scintillation detector.

That is, two different gamma lines, one from each of two different radiation sources, may be used to control the gain of the first scintillation detector, as described above.

For example, Am-241 and Ba-133 may be used. For example, Am-241 may be used to illuminate the scintillator by opening a lead shutter, or using a rotating lead disc with a small aperture. The latter option of a rotating lead disc with small aperture would imply a chopped response where data from the target of interest would be captured only when the Am-241 source is obscured by the lead plate.

The primary useful gamma emission lines with good penetrative power from these sources for the purposes of gamma Compton backscatter spectroscopy are:
- Am-241: 59.54 keV; and/or
- Ba-133: 80.997 keV and the closely adjacent much weaker 79.621 keV line; and/or
- Eu-152: 121.78 keV.

Particularly, the gamma emission lines for the purposes of gamma Compton backscatter spectroscopy need to be able to penetrate, with low attenuation loss, an external casing of an item under test in order to interrogate for the presence of a target, for example an explosive charge. Likewise the backscatter gamma from the explosive charge must be sufficiently penetrative to pass back through the casing with low attenuation loss.

Note that an NaI(TI) or CsI Scintillator detector lacks the spectral resolution to separately resolve the 80.997 keV and 79.621 keV lines. The 79.621 keV lines is a factor of approximately 12.7 times fainter than the 80.997 keV line. The measured spectral resolution of the 80.997 keV line by the NaI(TI) detector used herein is ~9.8% FWHM.

In addition the following emission lines may also be useful for gamma Compton backscatter spectroscopy:

Ba-133: 276.398 keV and/or 302.85 keV and/or 356.017 keV; and/or

Eu-152: 344.2785 keV.

For example, a Compton radiation backscatter detector may use Ba-133 sources placed directly in front of the first scintillator detector which emits several hard gamma at for example 356 keV that penetrate the lead shields that shield the scintillator detector from any significant direct transmission of lower energy gamma, e.g. 81 keV, from the Ba-133 radio-isotope sources. Advantageously, the breakthrough signal can be used to calibrate out the temperature drifts since the measured energy reading of the 356 keV gamma photons will drift in response to the temperature. This means that the scintillator detector's energy response may be continuously re-tuned in response to scintillator temperature changes thus preserving in real time the scintillator detector's energy calibration. This approach may be further extended to use for example a small Am-241 source to bleed 59.54 keV gammas into a conventional scintillator. Since Am-241 does not produce any significant harder gamma than 59.54 keV (at least with significant intensity), it would not affect the scintillator's utility when detecting higher energy gamma.

Controller

The scintillation detector assembly comprises the controller configured to control the gain of the first scintillation detector based, at least in part, on the first gamma radiation, having the first reference energy, detected by the first scintillation detector. In one example, the controller is configured to control gains of respective scintillation detectors of the set thereof based, at least in part, on the first gamma radiation, having the first reference energy, detected by the respective scintillation detectors. That is, the gains of the scintillation detectors may be controlled individually, for example. In this way, the gain of each scintillation detector may be controlled independently from the gains of the other scintillation detectors, thereby compensating for individual changes in temperature, efficiency and/or gain, for example. Additionally and/or alternatively, in one example, the controller is configured to control gains of respective scintillation detectors of the set thereof based, at least in part, on the first gamma radiation, having the first reference energy, detected by the set of scintillation detectors. That is, the gains of the scintillation detectors may be controlled together or in unison, for example. In this way, controlling the gains of the set of scintillation detectors may be simplified.

In one example, the controller is configured to control the gain of the first scintillation detector according to a temperature change of the first scintillator, a gain change of the first light sensor and/or an accuracy change of the first signal.

Shield

In one example, the scintillation detector assembly comprises a first radiation shield of a set of radiation shields, arranged to at most partially shield the first scintillation detector from the first radiation source. In this way, the first radiation shield attenuates (but does not entirely stop) the first gamma radiation radiated to the first scintillator, such that the first gamma radiation detected by the first scintillator is breakthrough radiation. The first radiation shield may completely stop lower energy gamma, for example 59.54 keV, 81 keV and/or 121.78 keV. In one example, the first radiation shield comprises and/or is a holder or housing for the first radiation source, having an aperture facing a target while at most partially shielding the first scintillator from the first radiation source. In one example designed for use with Am-241 gamma sources, the first radiation shield is provided by Pb, for example having a thickness in a range from 0.5 mm to 5 mm, preferably in a range from 1 mm to 4 mm, more preferably in a range from 2 mm to 3 mm, for example 2.5 mm. In one example, the set of radiation shields comprises T radiation shields, where T is a natural number greater than or equal to 1, for example 1, 2, 3, 4, 5, 6, 7, 8, 9, 10 or more. In one example, each radiation shield of the set thereof may be as described with respect to the first radiation shield. Conversely, in one example, one or more of the radiation shields may be different from the others of the set thereof, for example selected for the respective radiation sources, so as to permit breakthrough gamma radiation having different reference energies. In one example, the radiation shields of the set thereof are arranged regularly, for example in an array. In one example, each radiation source is associated with or housed in a separate radiation shield.

In one example, a narrow line gamma source is used to temperature correct the energy calibration of the first scintillator detector; for example even when lead shields are not being used. For example an Am-241 smoke detector source generates a strong 59.54 keV gamma line, as well as a few weaker lower energy gamma lines that themselves could be blocked with a very thin layer of absorbing metal say lead sheet. This source or sources could be placed on the side of the scintillator and the resulting total optical luminescence generated by the absorbed 59.54 keV line will give an indirect measurement of the scintillators temperature. The mapping between the channels number of the peak response obtained in the multi-channel analyser that reads the electrical signal from the scintillator detector's optical photomultiplier detector will provide a temperature correction function. Basically for example the Fine Gain of the detector systems digital read out can be adjusted to sit the peak response of the Am-241 59.54 keV line on the 'correct' channel of the multichannel analyser. The advantage of using Am-241 sources is that they are cheap, being a domestic smoke detector source, and they don't generate any hard gamma that are more energetic than 60 keV. The optical photomultiplier that reads the luminescence of the scintillator could be either a traditional vacuum tube photomultiplier or a solid state Silicon Photo-multiplier array.

Shutter

In one example, the scintillation detector assembly comprises a first radiation shutter of a set of radiation shutters, arrangeable in a first configuration to at least partially shield the first scintillation detector from the first radiation source and in a second configuration to expose the first scintillation detector to the first radiation source.

That is, the scintillation detector assembly may include a movable shutter or shield (i.e. the first radiation shutter), so that the first scintillation detector may be selectively exposed, for example at intervals such as before and/or after capture of a backscatter spectrum from a target and/or periodically, to the first radiation source and the gain thus controlled. The first radiation shutter and/or the set of radiation shutters may be otherwise as described with respect to the first radiation shield and the set of radiation shields, respectively.

In one example, the first radiation shutter is provided as or by a rotatable disc having one or more apertures therethrough. For example, Am-241 may be used to illuminate the scintillator by opening a lead shutter, or using a rotating lead disc with a small aperture. The latter option of a rotating lead disc with small aperture would imply a chopped response where data from the target of interest would be captured only when the Am-241 source is obscured by the lead plate.

Compton Radiation Backscatter Detector

The second aspect provides a Compton radiation backscatter detector comprising a scintillation detector assembly according to the first aspect.

Conventional Compton radiation backscatter detectors are known. Advantageously, gamma radiation for illuminating a target to acquire a Compton radiation backscatter spectrum thereof is additionally and/or alternatively used to control the gain of the scintillation detector.

Compton radiation scattering involves an incident gamma photon of energy $E_\gamma$ which is then scattered by electrons in the target material to yield a recoil electron, and a lower energy scattered gamma ray of energy $E_{\gamma'}$, and is given by:

$$E_{\gamma'} = \frac{E_\gamma E_0}{E_\gamma(1 - \cos\theta + E_0)}$$

where:

$E_{\gamma'}$ is the energy of the Compton scattered gamma photon;

$E_\gamma$ is the energy of the incident gamma photon emitted by one of the radio-isotope sources;

$E_0$ is the rest mass energy of the electron which is equal to 511 keV; and $\theta$ a polar angle that is referenced to the axis of travel of the incoming gamma photon, is the Compton scattering angle between the incident gamma photon and the scattered gamma photon.

Method of Controlling Scintillation Detector Assembly

The third aspect provides a method of controlling a scintillation detector assembly comprising a first scintillation detector of a set of scintillation detectors, comprising a first scintillator of a set of scintillators and a first light sensor of a set of respective light sensors optically coupled thereto, arranged to detect electromagnetic radiation, the method comprising:

detecting, by the first scintillation detector, first gamma radiation of a first set of gamma radiation, having a first reference energy of a set of first respective reference energies; and controlling a gain of the first scintillation detector based, at least in part, on the first gamma radiation, having the first reference energy, detected by the first scintillation detector.

The scintillation detector assembly may be as described with respect to the first aspect.

In one example, the method comprises at most partially shielding the first scintillation detector from the first gamma radiation.

In one example, the method comprises alternately at least partially shielding the first scintillation detector from the first gamma radiation and exposing the first scintillation detector from the first gamma radiation.

In one example, the method comprises:

determining a calibration for a spectrum, for example a Compton backscatter spectrum, using the first gamma radiation of the first set of gamma radiation, having the first reference energy of the first set of respective reference energies, detected by the first scintillation detector and optionally, using first gamma radiation of a second set of gamma radiation, having a first reference energy of a second set of respective reference energies, detected by the first scintillation detector.

In this way, an energy calibration of a MCA channel spectrum (i.e. a channel number to energy value number) may be determined for example, such as based on using the 59.54 keV line of Am-241 which is used to illuminate the scintillator crystal when the lead shutter is opened, and the 356.017 keV line of Ba-133 which breaks through the lead shield.

Particularly, the use of two or more gamma emission lines allows the variation in the scintillator's optical luminescence due to temperature or other effects, together with the separate drifts in the gain of the optical photomultiplier (or other optical detector), or separately drifts in the charge pulse measurement system, to be all calibrated out together.

Method of Detecting a Target using a Scintillation Detector Assembly

The fourth aspect provides a method of detecting a target using a scintillation detector assembly, the method comprising:

acquiring a background Compton backscatter spectrum and a Compton backscatter spectrum of the target; and background-subtracting the Compton backscatter spectrum of the target using the background Compton backscatter spectrum;

wherein the scintillation detector assembly is controlled according to the method the third aspect.

In one example, the method comprises acquiring a breakthrough spectrum. In one example, the method comprises subtracting the breakthrough spectrum from the Compton backscatter spectrum of the target. In one example, acquiring the background Compton backscatter spectrum comprises acquiring the background Compton backscatter spectrum and acquiring the breakthrough spectrum.

Use

The fifth aspect provides use of gamma radiation, having a reference energy, to control the gain of a scintillation detector comprising a scintillator and a light sensor optically coupled thereto.

The scintillation detector may be as described with respect to the first aspect. The control may be as described with respect to the third aspect or the fourth aspect.

Computer-Readable Storage Medium

The sixth aspect provides a tangible non-transient computer-readable storage medium having recorded thereon instructions which when implemented by a computer device comprising a processor and a memory, cause the computer device to perform a method according to the third aspect or the fourth aspect.

Definitions

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which.

DETAILED DESCRIPTION OF THE DRAWINGS

Figure 1:
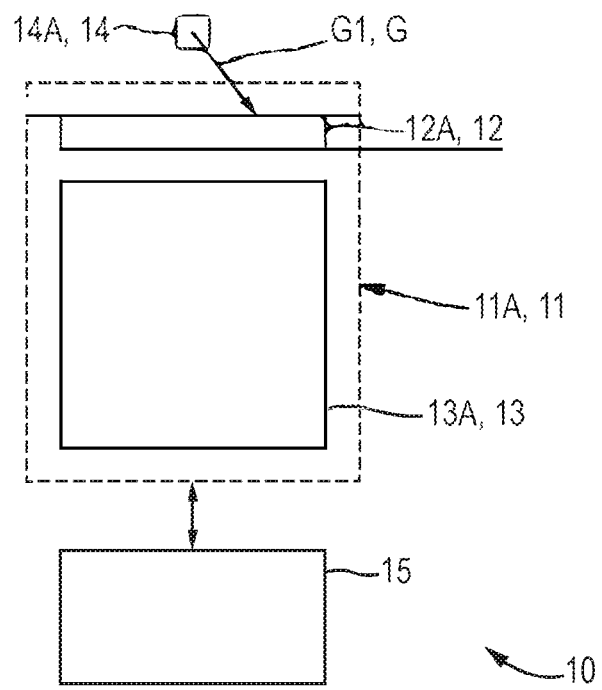
FIG. 1 shows schematically a scintillation detector assembly according to an exemplary embodiment.

FIG. 1 shows schematically a scintillation detector assembly 10 according to an exemplary embodiment.

The scintillation detector assembly 10 comprises:

a first scintillation detector 11A of a set SSD of scintillation detectors 11, comprising a first scintillator 12A of a set SS of scintillators 12 and a first light sensor 13A of a set SLS of respective light sensors 13 optically coupled thereto, arranged to detect electromagnetic radiation and output a first signal;

a first radiation source 14A of a set SRS of radiation sources 14, configured to emit first gamma radiation G1 of a first set SG of gamma radiation G, having a first reference energy RE1 of a set SRE of respective first reference energies RE; and a controller 15 configured to control a gain of the first scintillation detector 11A based, at least in part, on the first gamma radiation, having the first reference energy, detected by the first scintillation detector 11A.

The scintillation detector assembly 10 may be as described herein, for example with respect to the first aspect. The first scintillation detector 11A may be as described herein. The first scintillator 12A may be as described herein, for example as with respect to a scintillator 500 described below. The first light sensor 13A may be as described herein, for example as with respect to a SPAD 220 described below. The first radiation source 14A may be as described herein, for example as with respect to a source 110, 115 described below. The controller 15 may be as described herein, for example as with respect to a controller 325 described below.

Figure 2:
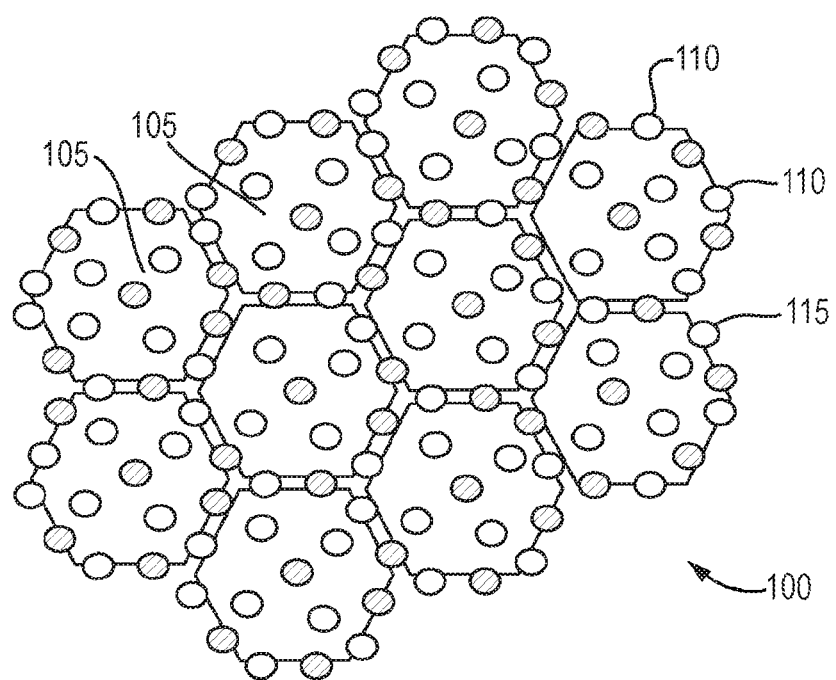
FIG. 2 shows a plan view of part of a tiled array of microcell detectors, including gamma sources for sample irradiation.
Figure 3:
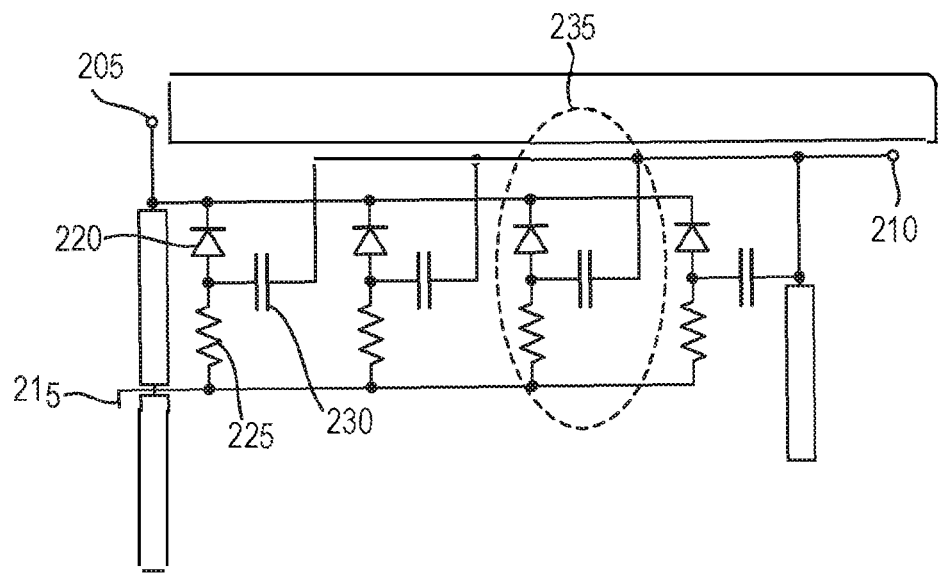
FIG. 3 shows schematic circuitry for a set of four microcell detectors based on avalanche photodiodes.

Referring to FIGS. 2 and 3, the backscatter radiation detector is based on an array 100 of microcell detectors in a tiled formation, in particular silicon photomultiplier detectors. Each tile 105 is contiguous with a number of other tiles and is provided with a plurality of gamma sources 110, 115 and has embedded in it a plurality of microcell detectors 235.

The gamma sources are evenly distributed about each tile 105 and comprise seven Ba-133 sources 110 (shown crosshatched) and ten Am-241 sources 115 (shown clear). Six of the barium sources 110 are spaced about the edge of each tile and one is placed centrally. Six of the americium sources 115 are also placed about the edge of each tile and four spaced evenly at a radius intermediate the centre and the edge. Sources 110, 115 along the edges of the tiles 105 are shared between contiguous tiles. This configuration of sources reduces the rate at which gamma flux falls with distance r from the source plane. By comparison, the gamma flux of a single point source decreases at a rate of approximately 1/r squared. Measurements with a lead shield and aluminium supporting structure, as described below in relation to FIG. 5, have shown that the backscatter signal level from a target layer fell only by a factor 2 with every approximately 15.5 mm increase in range.

Regarding the sources 110, 115, these are radioisotope sources which generate a number of discreet photon energies. For example Am-241 (Am-241) emits gamma at 59.54 keV, 26.34 keV and 13.9 keV as well as at a number of other discrete photon energies, although the branching ratio for emission of these other photon energies is negligible compared with the three lines quoted. The Ba-133 sources provide higher gamma emission energies than the AM-241 sources, for example 81 keV, 302 keV, and 356 keV as well 6 other much weaker gamma emission lines. There are also two strong X-ray lines at 30.973 keV and 30.625 keV due to atomic transitions in the electronical excited Cs daughter atom formed by the decay of Ba-133.

The gamma source array configuration, in the embodiment being described, might then consist of:
- ten or twelve sealed Am-241 sources of activity 29.6 kBq (+/−20%)
- seven sealed Ba-133 sources of activity 100 kBq (+20%/−10%), or sealed Eu-152 sources of activity 100 kBq (+20%/−10%)

The Am-241 sources are supplied by High Tech Sources Limited (part number AMMK7650) and the Ba-133 sources are supplied by Eurostandard Cz (part number GBa3.11).

A further potential source for embodiments of the invention is Eu-152, in particular the 121.78 keV gamma emission line of Eu-152 (Eu-152). Sealed Eu-152 sources are also supplied by Eurostandard Cz (part number GEu2.11).

It has been noted that the 26.34 keV gamma line of Am-241 has been found to be significantly attenuated by the materials found in a typical tablet or laptop and thus may not be ideal for embodiments of the invention, depending on the intended application. Preferred from this point of view might be the gamma ray emission lines emitted by Ba-133 (Ba-133) or possibly Eu-152 (Eu-152), as well as the 59.54 keV line of Am-241. Retaining the Am-241 59.54 keV offers significant benefits as it enables aluminium to be discriminated from real explosive compounds. Aluminium is an energetic material which when added as a powder to the fertilizer ammonium nitrate, forms a secondary high explosive. Aluminium significantly attenuates the 59.54 keV line and its ~50 keV backscatter line if a thick plate (~5 mm) of aluminium is being transited. By comparison the 81 keV gamma line and its ~62 keV backscatter line does not exhibit this attenuation. An explosive like RDZ, TNT or PETN does not exhibit this attenuation feature.

The radioactive half-lives of the three radio-isotopes Am-241, Ba-133 and Eu-152 vary considerably with values of 432.6 years, 10.51 years and 13.517 years, respectively. A recommended working lifetime for the Ba-133 and Eu-152 sources is 15 years. The impact of the relative variation in the activity of the source over time due to the significantly low half-life of either Ba-133 or Eu-152 on the resulting gamma backscatter spectra intensity may need to be compensated for computationally.

Although other isotopes of other elements might be found useful, only Am-241, Ba-133 and Eu-152 are currently proven to be useful for embodiments of the present invention. For example of the nineteen isotopes of Am, only three have significant lifetimes (all the rest have half-lives of less than a day), and only Am-241 emits a useful gamma for the current application. However Eu-152 is less suitable than Ba-133 or Am-241 as its very hard gamma emission line radiation is hard to block requiring a much thicker layer of lead to block it. For example, 3.8 cm of lead is required for Eu-152 to reduce the overall radiation dose by a factor 10 c.f. 0.7 cm of lead for Ba-133 to reduce the radiation does by a factor of 10. Alternatively the Compton Backscatter detection system in which it is used would need a much larger exclusion volume to prevent operator exposure to a legally significant radiation dose. The IRR17 regulations require any system's radiation dose rate exposure on all accessible surfaces to less than 1 µSv/hour for innocent bystanders who are not radiation workers with formal radiation awareness training. The radiation dose limit for radiation trained workers is 7.5 µSv/hour whole body dose before special control measures have to be put in place. Also the various hard gamma emitted above 400 keV by Eu-152 create a nearly white background spectrum due to multiple Compton Scattering events. This stochastic noise due to this background white spectrum would reduce the sensitivity of the system.

FIG. 3 shows four microcell detectors 235 as they would be connected on a tile 105 (not shown). Each microcell detector 235 comprises a single photon avalanche photodiode (SPAD) 220 connected with a quench resistor 225 between a cathode 205 and an anode 215. All the microcell detectors are connected via a fast output capacitor 230 to a tile output 210.

Tiled arrays of microcell detectors of this type are supplied by SensL Technologies Ltd. A tiled array lends itself to supporting a suitable arrangement of source components which can be placed along or between the edges of the tiles.

Figure 5:
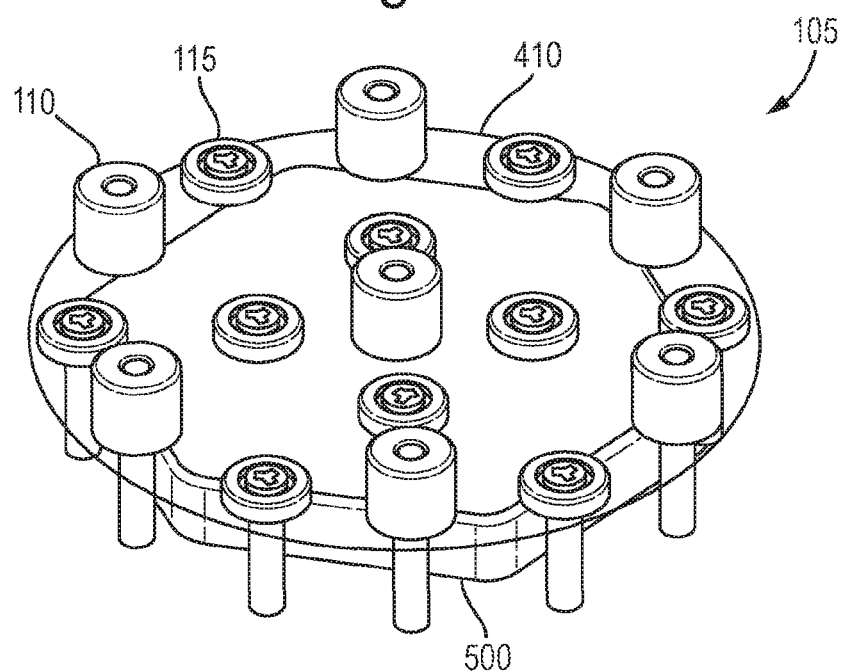
FIG. 5 shows a set of radiation sources.

Referring to FIG. 5, each detector tile 105 consists of a tile 500 of scintillator crystal (could be a plastic although this is less efficient) which on its rear (large) surface is bonded an array(s) of SPADs 220. The SPAD can alternatively be placed on the flat side faces of the tile provided it is thick enough; a 20 mm thick tile is fine for this purpose. Except where the SPADs 220 are bonded with an optically transparent adhesive, the polished surfaces, including the edges, of the scintillator tiles are coated with a high reflectivity coating. This ensures that any optical photons generated within the scintillator by an absorbed gamma photon are guided to encounter an individual SPAD 220 and cause it to fire generating a charge pulse. (This ignores the impact of any optical losses at the reflective coatings.)

Regarding dimensions, options are either to use a set of detector tiles 100 so that no moving detector array is needed, the dimension of each tile being such as to provide a preferred resolution in terms of finding a threat material 320 in the sample 300, or alternatively to use a scintillator detector on a 2-D scanning system. An issue then would be the time taken overall, based on the time to scan at each position before moving on to the next scan position.

An example of an americium radioisotope source component 115 (Am-241) comprises americium material mounted on a 2 mm thick disc shaped lead or tungsten shield of diameter 8 mm to protect the detector array from direct irradiation. These discs have been found extremely effective, for example suppressing transmission of the 59.43 keV (sometimes referred to as 60 keV) gamma line by about 99.993%. The sources 115 are then supported on the scintillator layer 305, optionally via an intervening support layer of aluminium 410.

Each of the Ba-133 sources would be placed on a 7 mm thick lead disc shield 405 of diameter 10 mm to provide direct line of sight shielding between the sources and the scintillator. Suppression of the 81 keV emission line would be approximately 100%, while suppression of the 276 keV gamma emission line of Ba-133 would be greater than 94.6% (percentage of incident gamma that would be subject to the Photoelectric absorption process alone).

An alternative option to the Ba-133 sources is sealed Eu-152 sources which may provide tangible performance benefits in terms of penetrative capability. Eu-152 would preferably be provided with thicker shielding than Ba-133 sources but 7 mm lead is acceptable in practice, provided the total gamma detection rate is less than the ~95% coincidence free detection rate; which it was for our detector arrangement. This figure refers to coincidence detection events where the nearly decayed luminescence pulse from a previous gamma detection event is more than 1/e squared of the next gamma detection event. The choice of a 95% maximum coincidence free detection rate is a matter of subjective judgment. Another option would be to use tungsten which offers moderately better absorption performance than lead, although machining this material is difficult and costly. Another option again would be to use gold as a shielding material, although this option would be very expensive and so not practical from a commercial perspective.

Figure 6:
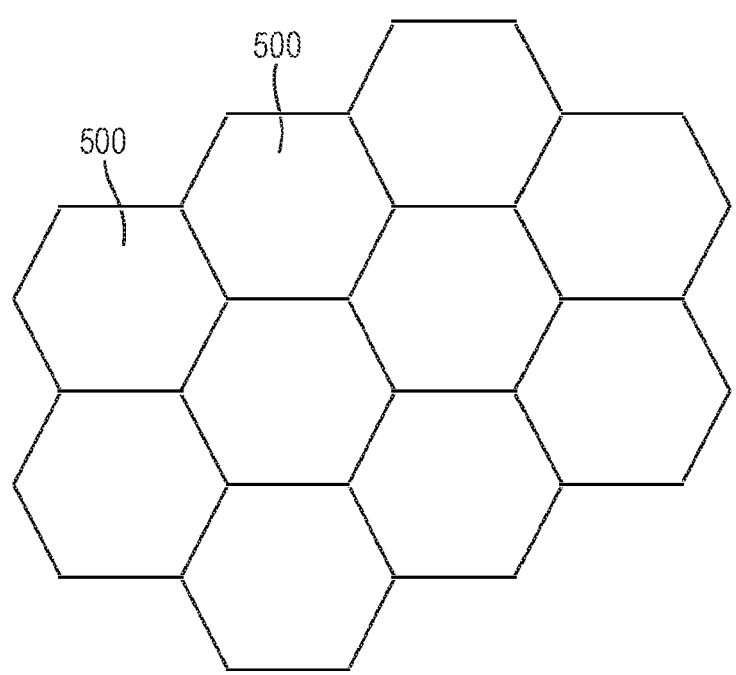
FIG. 6 shows a hexagonal array of scintillation material for use in the tiled array of FIG. 2.

Referring additionally to FIG. 6, the scintillator layer is a tiled array of hexagonal scintillator crystals 500, each of thickness approximately 20 mm, the array covering a footprint equal to that of a typical laptop, approximately 400 mm×250 mm. Each scintillator crystal 500 would correspond to a tile 105 of the tiled array 100 for detecting the scintillation pulses. A suitable type of scintillator is described at https://www.crystals.saint-gobain.com/products/pixellated-arrays, these arrays being supplied by Saint-Gobain Crystals which is a business of Saint-Gobain Ceramics. Saint-Gobain provides for example 20 pixelated array assemblies for use in medical scanners, and linear arrays which are used for airport baggage scanners. Saint-Gobain has also published useful tables on the performance properties of various scintillator crystals. Typically, Nai(TI) might be used which is a well-established, relatively 'cheap' material albeit slower than Lanthanum Chloride (BrillanceCe™ 350). It has a relatively good yield of approximately 38 optical photons at a centre wavelength of approximately 415 nm for every keV of absorbed photoelectron energy. The downside of this material is that the decay time for the optical scintillation pulse is quite long at 250 ns (the 1/e value). This means the average detected count rate must be less 1/250 ns, i.e. less than approximately 4 million counts per second. However this count rate limit does not take into account the impact of shot noise statistics which predict for a given count rate the probability of the number of optical pulse coincidence events where two gamma rays are detected within the approximately 250 ns decay time. Therefore in practice the rate at which counts due to a single gamma photon absorption event are reliably resolved using NaI(TI) will be significantly less than 4 million counts per second.

Regarding the distribution of the sources 110, 115 over the face of the source/tiled array 100, this is now described in relation to FIGS. 2, 5 and 6.

Ideally, the sources 110, 115 would be spread uniformly across the surface and along the edges of the scintillator tiles 500. With regard to the distribution of sources 110, 115 around the edges of the tiles 105, or across the surface, this should be as symmetrical as possible for the number of sources of each type.

The diameter of the disc shields 405 needs to be sufficiently large that the direct line of sight of the from the gamma source to any point across the scintillator crystal 500 has a sufficient path length in the shielding material to stop any direct gamma transmission. For the 59.54 keV line of Am-241 or the 81 keV line of Ba-133, a 2 mm transmission path through lead (which stops about ~99.99% of incident gamma at 60 keV) is more than sufficient. The source geometry, namely its radio-isotope height relative to the base of the source package that sits directly on the shield 405, combined with the energy of the gamma photons of interest, in general determine the minimum diameter for the shield required.

The maximum number of sources 110, 115 that can be accommodated is a judgement call. The more sources 110, 115 that are placed on a tile 105, either around its periphery or on its top surface, the larger the fractional area which will be 'blind' to Compton backscattered photons. As an example, using fifteen Am-241 sources 115 in the geometry shown in FIG. 1, if the total top surface area of the tiled array 100 is nominally defined by a circle of area 4560 mm$^2$, the area of lead shields 405 each of 10 mm diameter was approximately 1178 mm$^2$. So to first order, 25.8% of the array aperture was obscured, ignoring shadowing caused by the height of the lead discs 405 and also the impact of the angular intensity distribution of the Compton backscattered photons. The result was a geometry that worked well with the disc shields not substantially increasing the integration time needed to get sufficient counts to suppress the impact of shot noise statistics (i.e. root n/n noise) on the final result. As an estimate, it might be reasonable to increase the number of sources 115 until the area of the scintillator or detector tile 500, 105 obscured by the associated gamma shield (discs 405) of each source occupies about half the tile's surface area.

With regard to the total activity of the different source types, this should be biased in favour of the higher energy sources as the Compton effect falls off with increasing gamma energy. Ideally one wants nominally equal numbers of backscattered photons from each of the gamma emission lines as this will give the best shot noise (root n over n) statistics in terms of stable count rates per individual measurement.

Finally in regard the distance to the target, this again is a trade-off. In the specific case of the prototype geometry with fifteen Am-241 sources which were distributed at substantially equal spacing across the 76.2 mm diameter aperture of the scintillator detector, it was found that the Compton backscatter signal fell off at the rate of about a factor two every ~15.5 mm of increased height. So the target should ideally be placed as close to the sources 110, 115 as possible to minimise the time taken to achieve good shot noise statistics on the count rate within given energy bands.

Regarding mounting of the sources 110, 115 on the detector array 100, their shielding discs (or cups) 405 can be bonded directly to the top surface of the scintillator material 500 for the sources which are not placed around the edges of the tiles 105. However, it might be preferred to bond the sources 110, 115 to a thin aluminium sheet 410 of for example 0.2 mm thickness. This thin aluminium sheet 410 would be placed on the top surface of the scintillator tiles 500. This way the sources can be removed if necessary, without having to throw away for example the scintillator tile and associated SPAD arrays bonded to it. The scintillator tiles 500 are provided with a highly reflective coating. Mounting the sources 110, 115 via an Al sheet avoids potential ill effects of bonding directly to this reflective surface. One mounting option would be for holes to be drilled through the aluminium sheet 410, and mounting rods to pass through them to locate the aluminium sheet 410.

Figure 4:
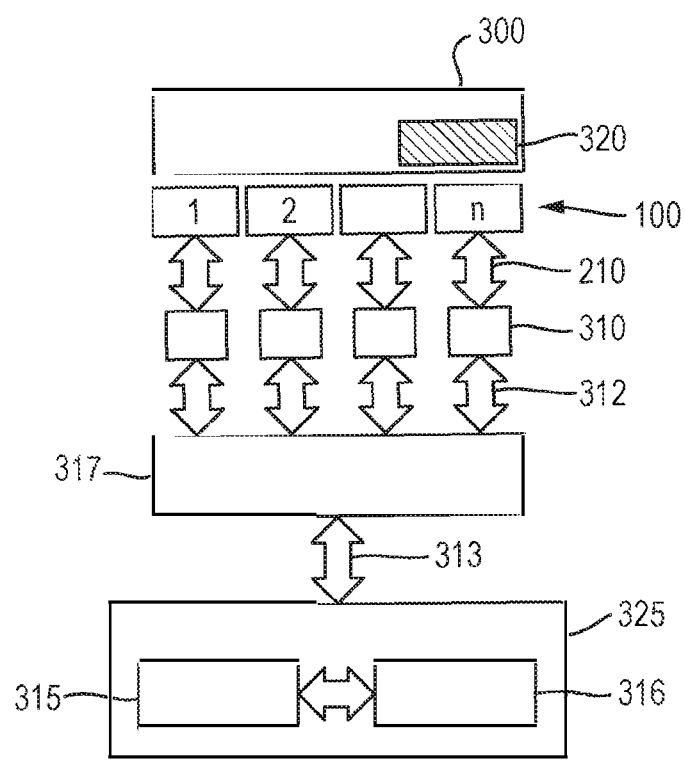
FIG. 4 shows a schematic block diagram of a backscatter radiation detector assembly according to an exemplary embodiment.

Referring to FIGS. 2 and 4, a sample such as an electrical device 300 under test would be placed directly over the source/tiled array 100. Preferably this might be achieved by loading the device 300 in a frame that can then be moved remotely into position over the source array 100 in order to avoid user exposure to the sources 110, 115. Gamma radiation emitted by the sources 110, 115 will pass through the device 300 and a small percentage (approximately 2% at ~60 keV from an approximately 5 mm thick explosive sample) of the incident radiation is backscattered, back towards the sources 110, 115 and the scintillator-based detector tile array 100 beneath them. The backscattered gamma photons generate photoelectrons inside the scintillator crystal layer, which in turn generate pulses of light linearly proportional to the energy of the individual absorbed gamma. The SPADs of the tiled array 100 detect each light pulse and generate a highly amplified electrical current pulse of total charge proportional to the respectively detected light pulse energy. These charge pulses are channelized by a multi-channel processor 310. This channelized digitised data is then transferred to a data collection software package as the event collator 315. An example is eMORPHO, provided by Saint Gobain referred to above.

Signal crosstalk between tiles 105 will generally be low since optically they are completely isolated from one another. The scintillator crystal is coated with a high reflectivity surface, in the visible spectrum, so that photons hitting the sides of the scintillator will typically multiply reflect until eventually the photons impinge on one of the optical detectors of the SPAD array and are absorbed. Gamma photons are completely absorbed by a photoelectric absorption event in a given scintillator crystal or not at all. However, energy can be coupled from the gamma photon to a recoil electron in the scintillator material if a Compton scattering process occurs. For example, in the specific case of Compton scattering of a 60 keV gamma photon, the energy transferred to the recoil electron will vary between 0 keV and maximum of 11.24 keV (the retro-reflection case). The deflected lower energy gamma ray may then be either absorbed in a subsequent photo-absorption event, scattered in another Compton scattering process in which case less energy is transferred on average to the recoil electron, or finally exit the scintillator tile. Gamma photons that interacted with two different tiles through a combination of Compton scattering events, and then possibly a subsequent photo-absorption event, would yield gamma energies smaller than those absorbed solely in a single tile, so could be discriminated against.

Referring to FIG. 4, the tiled array 100 of FIG. 2 is arranged below a sample 300 to be scanned, such as a "device under test"; a laptop or the like, within which a threat material 320 is hidden. The sample/device 300 is placed over the array of detector tiles 105, 1 to n.

Each SPAD array(s) 100 on a given detector tile 105 is connected to a charge pulse bus 210 which transmits the charge pulses associated with each absorbed photon to a corresponding multi-channel analyser 310 (MCA). This MCA 310 could alternatively be a dual or more channel analyser. The MCA 310 collects all of the charge pulses associated with a gamma absorption event and channelizes the collected charge to yield a detected gamma energy value, which is digitised and then transmitted to a hub 317 via a digital data bus 312 that is associated with the particular MCA 310. The purpose of the hub 317 is to route all of the digital signals from the set of MCAs 310 to a controller 325, which typically may be a laptop computer, via a further data bus 313. The further data bus 313 can be USB-based, Ethernet, or another appropriate digital bus technology. A USB hub 317 for example can support 127 USB inputs 312 to a single USB output 313.

Within the controller 325 is located an event correlator 315 responsible for data collection, data analysis and threat status determination. Also within the controller 325 there is a network controller 316 to control data flows through the network of digital links.

Referring additionally to FIGS. 2 and 3, in use, backscattered gamma photons generated originally by the gamma sources 110, 115 may produce a burst of scintillation photons in the scintillator layer 305 of the detector array 100.

Each SPAD 220 that detects a scintillation photon or photons emitted within its respective tile 105 will generate a highly amplified charge pulse through the electron avalanche effect. This charge emerges as a pulse through the tile's signal line 210. Other SPADS 220 of the same tile likewise dump charge pulses onto the same signal output line 210. Summing all of the charge of the charge pulses within a suitable gated time window yields a figure for the total energy dumped into the scintillator crystal by an individual absorbed gamma and then detected in a tile 105. Summing might for instance be done by measuring the voltage drop across a resistor through which the charge pulses pass. The output current from the tile therefore indicates the photon flux resulting from a backscattered gamma photon. The length of the gated time window required will be dependent on the relaxation time of the scintillator crystal material and must exceed it. For Nai(TI) this relaxation time is quite long at 250 ns.

The total summed charge pulse is then passed to a multichannel or dual channel analyser (MCA/DCA) 310 to effect a determination of the energy of the original absorbed gamma which would have released a large number of scintillation photons at approximately the same time. Thus the output from each individual tile 105 will be passed to its own MCA/DCA 310.

The energy of a backscattered gamma photon is determined by measuring the total optical pulse energy associated with every photoelectron event associated with the absorption of a gamma photon. The total optical pulse energy here is for its part determined by measuring the total charge released by the charge avalanche events within the SPADs 220 attached to the scintillator layer 305 of a given tile 105 of the array.

The use of a tiled array 100 means that if a suspect device 300 is placed over it and threat material 320 is very localised, then the selected tile(s) 105 over which the threat material 320 is placed will yield a greatly enhanced signal relative to other tiles 105, giving significantly more information than would be the case if all the signals from different detectors were simply added together.

Further, the sources 110, 115 can be placed on the edges of each tile 105 and so will provide gamma radiation for either a pair of tiles (adjacent tiles) or three tiles (where three tiles 105 meet).

Experimental

Figure 7:
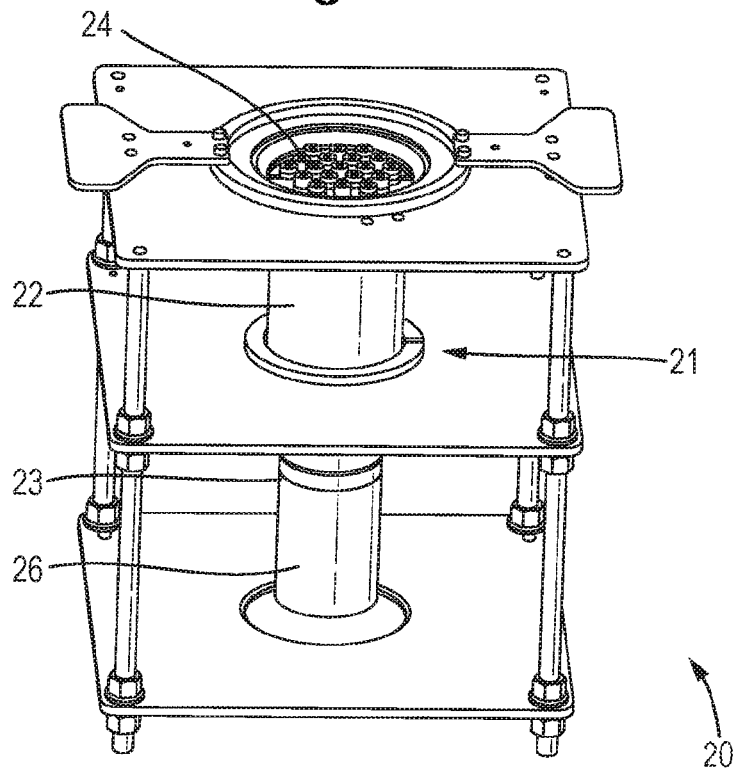
FIG. 7 shows a 3D model of a Compton radiation backscatter detector according to an exemplary embodiment.

FIG. 7 shows a 3D model of a Compton radiation backscatter detector 20 according to an exemplary embodiment. In this example, the Compton radiation backscatter detector 20 comprises a set of scintillation detectors 21, comprising a set of scintillators 22 and a set of respective light sensors 23 optically coupled thereto, arranged to detect electromagnetic radiation and output a first signal, a set of radiation sources 24, configured to emit a first set of gamma radiation, having a set of respective first reference energies; and a controller 25 configured to control a gain of the set of scintillation detectors 21. In this example, the Compton radiation backscatter detector 20 comprises a MCA 26. The set of scintillators 22 is provided by NaI(TI) of 3" (76.2 mm) diameter and 3" (76.2 mm) height, particularly a Saint Gobain scintillator detector, model number 3M3/3 NaI(TI). The set of radiation sources 24 is provided by 12 off Am-241 sources and 7 off Ba-133 sources.

Figure 8:
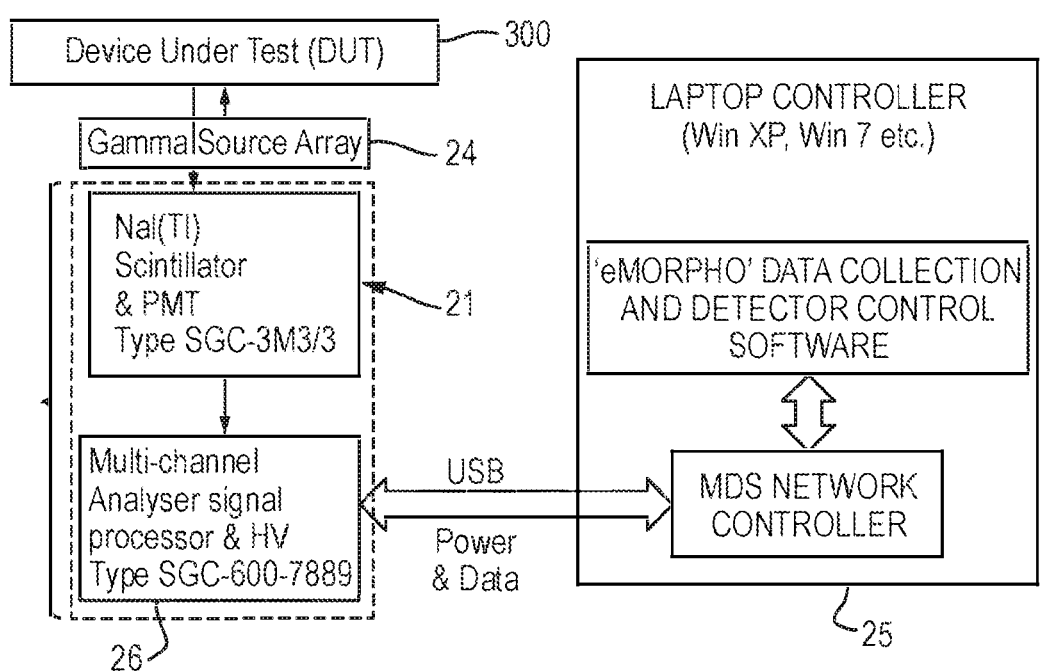
FIG. 8 shows a block diagram of a data capture system for the Compton radiation backscatter detector.

FIG. 8 shows a block diagram of a data capture system (i.e. the controller 25) for the Compton radiation backscatter detector 20.

Figure 9:
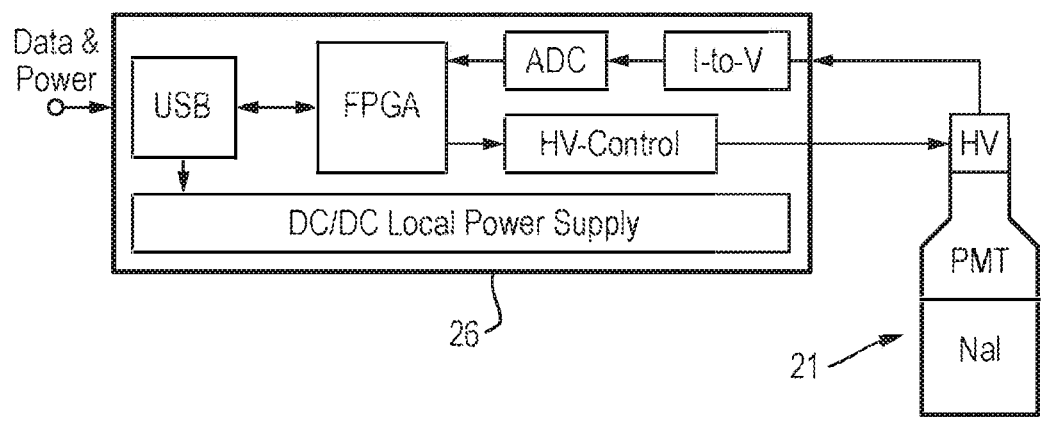
FIG. 9 shows a block diagram of a Multi-Channel Analyser and a scintillation detector.

FIG. 9 shows a block diagram of an 'eMORPHO' Multi-Channel Analyser Unit SGC-600-7889 26 and the scintillation detector 21.

The radiation sources are mounted on separate aluminium mounting spiders, as shown in FIG. 7. Each source is mounted inside an open ended cup of lead. The primary purpose of this lead shield is to suppress the direct transmission of emitted gamma rays from the radio-isotope source to the scintillator detector used to detect backscattered gamma photons. In practice some of the gamma emission lines of both Ba-133 and Eu-152 are so energetic that they will be partly transmitted though the lead shields. For example >11.9% and >15.8% of the 356 keV and 383 keV gamma emission lines of Ba-133 will respectively transmit through a 7 mm thick lead shield. In the case of Eu-152 the lead shield will be relatively ineffective at stopping many of the higher gamma emission line energies of Eu-152. For example, for Eu-152, >10.3% of the 344.3 keV emission line will pass through the shield's 7 mm thick base and >66.3% of the 1408 keV emission line will pass through the shield's 7 mm thick base. Eu-152 has a total of 5 significant gamma lines with energies greater than 345 keV that have branching ratios greater than 10%, as well as numerous other high energy gamma emission lines with a lower branching ratio than 10%. Consequently direct transmission of these higher energy gamma lines from the source to the detector will occur. These higher energy gamma lines provide the reference gamma radiation, as described herein. Nevertheless these partially transmitted gamma emission lines remain usable by the explosive detection system. This is because the energy of the Compton backscattered gamma photons all lay well outside the detectable spectral linewidth of the gamma emission lines.

A Saint Gobain scintillator detector, model number 3M3/3 NaI(TI), is used. This detector has a 76.2 mm (3") diameter by 76.2 mm cylinder of thallium doped Sodium Iodide single crystal as the scintillator medium. NaI(TI) single crystal scintillators have a very high luminescence efficiency; it yields approximately 38 photons per keV of absorbed gamma energy with the peak in the optical luminescence occurring at ~415 nm. As such it is well matched to sensitivity curve of photomultiplier tubes that are optically interfaced to the base of the scintillator. Approximately $10^4$ photoelectrons per MeV of absorbed gamma energy are produced by the scintillator. These photoelectrons have an average wavelength ~415 nm which are detected by a vacuum photo-multiplier tube optically bonded to the base of the scintillator crystal. The amplified photoelectron charge pulses from the photomultiplier are first integrated to yield a total charge indicative of the energy of the photo-absorbed gamma. The measured charge is then channelized into gamma energy bins by a multi-channel analyser attached to the base of the scintillator detector. This MCA then digitises the data and then transfers it to computer for data storage and subsequent analysis. The scintillator crystal in the detector is located inside a light tight aluminium case with a 1 mm thick aluminium window of diameter ~79.7 mm on its input detector surface.

For Silicon Photomultiplier (SiPM) detectors, the luminescence peak of the scintillator CsI in the yellow is better suited to the spectral response than NaI(TI) scintillators. CsI is also much more rugged to both mechanical and thermal shock than NaI(TI). So CsI combined with SiPM is a better combination than NaI(TI) and SiPM.

The photoelectron pulses generated by each gamma absorption event are detected and the total charge within the pulse event is summed. The charge is then channelized into one of up to 4097 discrete energy bins by the SGC-600-7889 multi-channel analyser attached directly to the base of the scintillator detector. This unit also generates the high voltage used to power the chain of charge multiplying dynodes of the photomultiplier tube which is attached to the base of the scintillator crystal.

Referring to FIG. 8, the digitised data created within the multi-channel analyser is sent by a USB data link to a laptop computer where it is then processed by the eMORPHO Data collection and detector control software. This data collection software generates an .xml file which lists as a list of sequential numbers the number of counts in each energy channel created by the multi-channel analyser. The data file also includes other key information such as for example:

The date of the measurement;
The spectrum integration time;
The setup configuration for the photomultiplier and the multichannel analyser;
Total number of detected gamma detection events;
The centroid energy value of an operator designated detected gamma line;
The FWHM of the selected gamma line; and
The number of detection events within a given energy span.

This file can read directly into MATLAB or alternatively opened as a text file which can be cut and pasted into an EXCEL spreadsheet for subsequent more detailed data analysis.

On the top of the scintillator detector shown in FIG. 7 are located an array of gamma sources 24. Each source is mounted inside its own lead shield. The different shielded gamma sources are then mounted on different aluminium mounting spiders which can hold respectively 12 off Am-241 sources, 7 off Ba-133 sources and finally a single Eu-152 source. This mounting approach allows different combinations of source configurations to be set up rapidly and safely without having to remove and remount the sources on the spiders. The lead shields are designed to prevent direct transmission of gamma from the sources to the scintillator detector at the gamma energies of particular interest to the Compton backscatter spectroscopy measurements, i.e. those below ~160 keV.

Smaller test pieces for gamma spectroscopy measurements can be mounted inside the sample holder shown in FIG. 7; its 0.5 mm thick aluminium base has been removed from this solid model image to allow the source array to be seen. Larger test pieces will be placed directly onto the top surface of the top plate of the test rig with the sample holder removed; engineering slips are used to offset precisely the bottom surface of the test samples above the source array prior to capturing gamma backscatter spectrum.

Gamma spectra will be captured with short integration times of 5 seconds or less as well as relatively long integration times of one minute, or indeed even longer integration times if required. The longer integration times will reduce the impact of shot noise on the captured spectra due to the random stochastic process of gamma emission where total count values n in any given energy channel bin can be expected to exhibit a root n over n statistical variation. The high resolution low noise data will allow the characteristic spectral features of the explosive material RDX/Wax to be discerned with greater ease in the subsequent data analysis work package. The shorter integration time data will then be used to establish and demonstrate a minimum required integration time required to reliably detect an explosive sample.

Post Spectral Data Capture Analysis

Analysis software can for example be implemented in MATLAB to automatically extract characteristic features from the gamma spectra across all observed energy bands. Other computational software can be used in place of MATLAB. The aim is to identify features indicative of the presence of a high explosive compound. Data can be recorded for different spectral capture integration times and then analysed to detect the minimum time required to provide sufficient signal to noise to detect the discriminating features for a given mass of the target explosive compound; example include RDX/Wax 93/7, TNT or PETN.

Each spectral data series would be read pre-processed and the following features would be recorded:
1. Peak signal values
2. Peak energy positions
3. Local spectral energy spread around the energy peaks.
4. Count numbers of the main Compton Backscatter spectral band associated with each gamma emission line.

The main Compton backscatter spectral band corresponds to the energy range of the detected backscattered gamma photon where only a single Compton scattering event for that photon has occurred in total.

Data analysis will apply techniques such as low pass filtering, data mining, clustering and others to minimise false alarms and false passes.

Results

Figure 10:
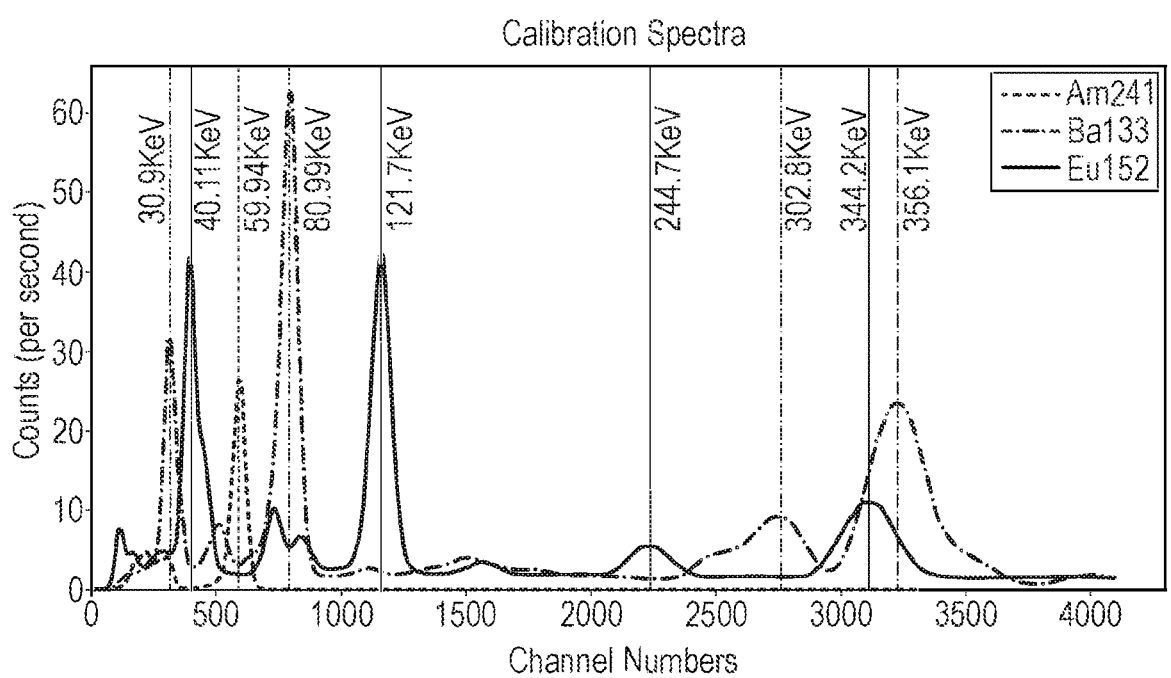
FIG. 10 shows examples of emission spectra of Am-241, Ba-133 and Eu-152 with energy represented by channel numbers with values ranging from 0 to 4000.

FIG. 10 shows examples of emission spectra of Am-241, Ba-133 and Eu-152.

Particularly, FIG. 10 shows examples of the emission spectra of Am-241, Ba-133 and Eu-152, in units of counts, plotted as a function of channel number rather than keV (i.e. energy).

Figure 11:
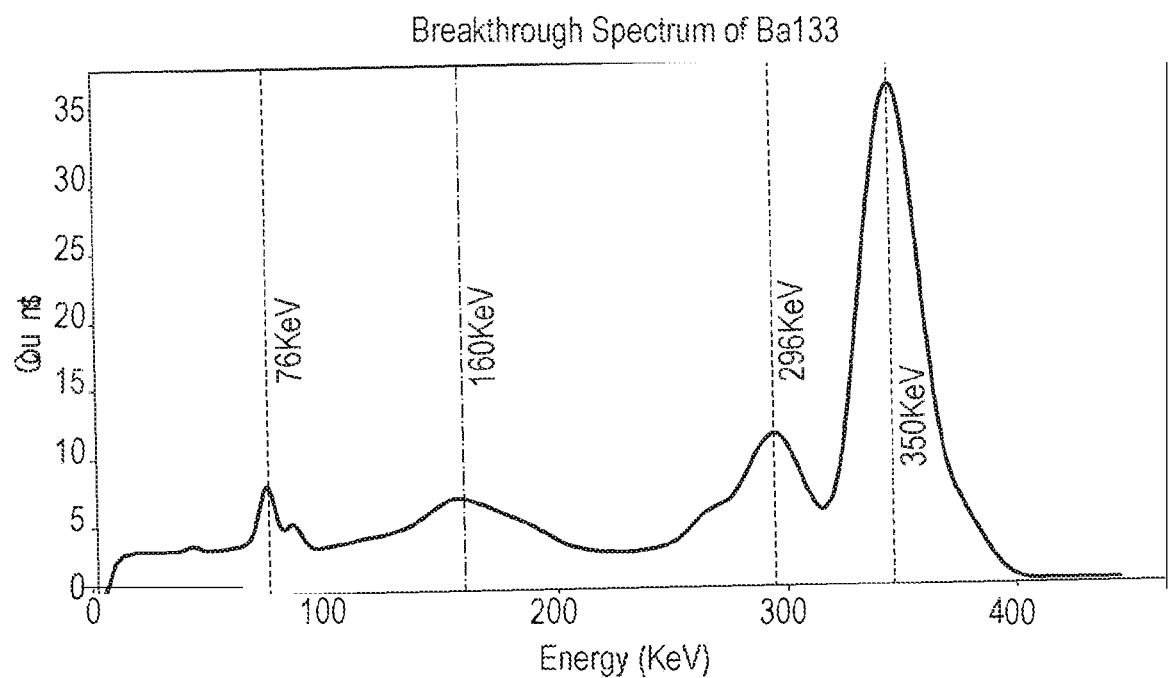
FIG. 11 shows an example of a breakthrough gamma signal due to Ba-133 observed through a lead shield with energy represented in keV from 0 to 400.

FIG. 11 shows an example of a breakthrough gamma signal due to Ba-133 observed through a lead shield.

Particularly, FIG. 11 shows an example of breakthrough gamma signal due to Ba-133 observed through the lead shields on the scintillator detector in counts per second per energy channel, for a total of 4097 energy channels of the MCA. Channel here refers to the individual energy channels of the MCA. Although the number of counts per second in each channel is relatively small, integrating the counts over a large number of channels dramatically improves the shot noise statistics (root n over n noise). The data are captured in the form of counts per channel for a given signal integration time. This data are then converted in to Counts per second per energy channel by using the channel to energy mapping function, and dividing the counts per energy channel by the integration time. Note how the breakthrough spectrum falls to ~0 at high energies, because the highest energy gamma emitted by Ba-133 is at 383.8 keV. Consequently there is no Compton 'white' noise caused by multiple Compton scattering events at energies above 383.8 keV.

Figure 12:
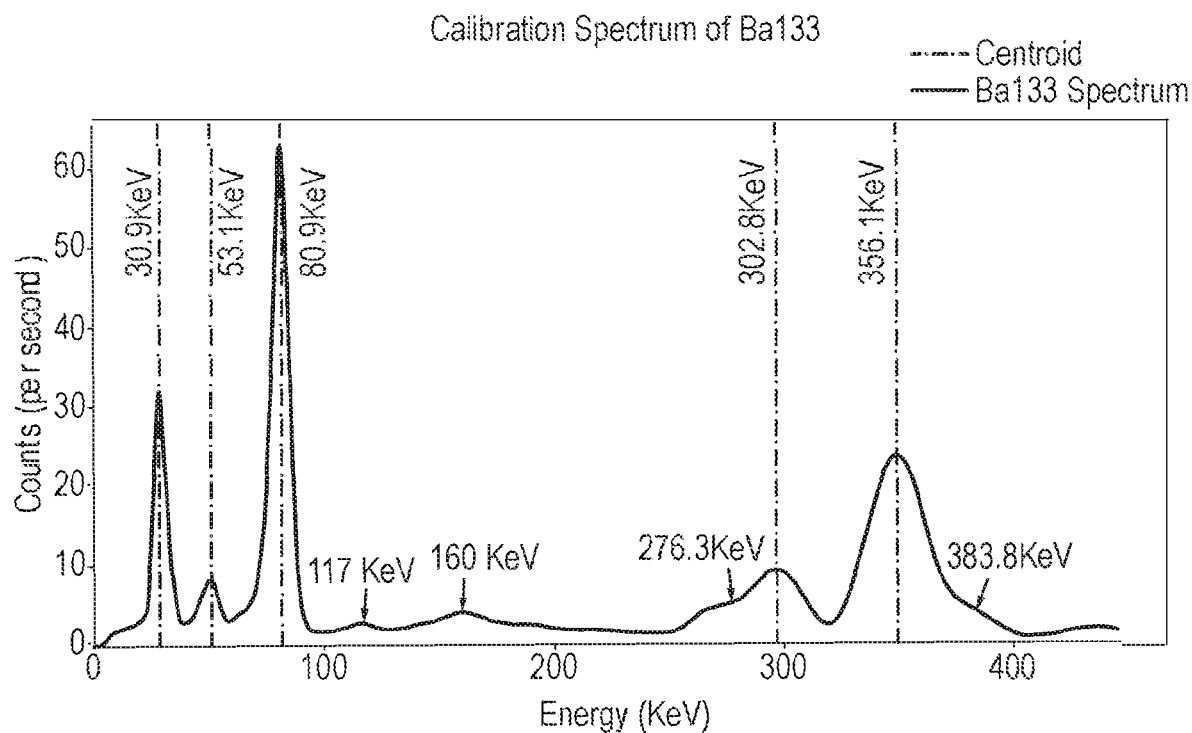
FIG. 12 shows an example of a breakthrough gamma signal due to Ba-133 and Am-241 observed through a lead shield with energy represented in keV with values ranging from 0 to 400.

FIG. 12 shows an example of a gamma emission spectrum of Ba-133 over the energy range 0 to >400 keV after subtracting away the natural background radiation. This spectrum is prior to converting from MCA channels to Energy channels was used along with a Am-241 spectrum and a Eu-152 spectrum to determine the mapping between channel numbers and energy value. This is a Barium-133 emission spectrum, where a single Ba-133 source in its lead shield was placed at a stand-off position over the scintillator detector and facing towards the scintillator. No other sources are present. The weak broad spectral features at ~160 keV is believed to be due to backscatter gamma generated by the 356 keV and 383.8 keV gamma emission lines of Ba-133. The even weaker broad feature at 117 keV may be due to the backscatter of the 302.8 keV gamma emission line of Ba-133

Figure 18:
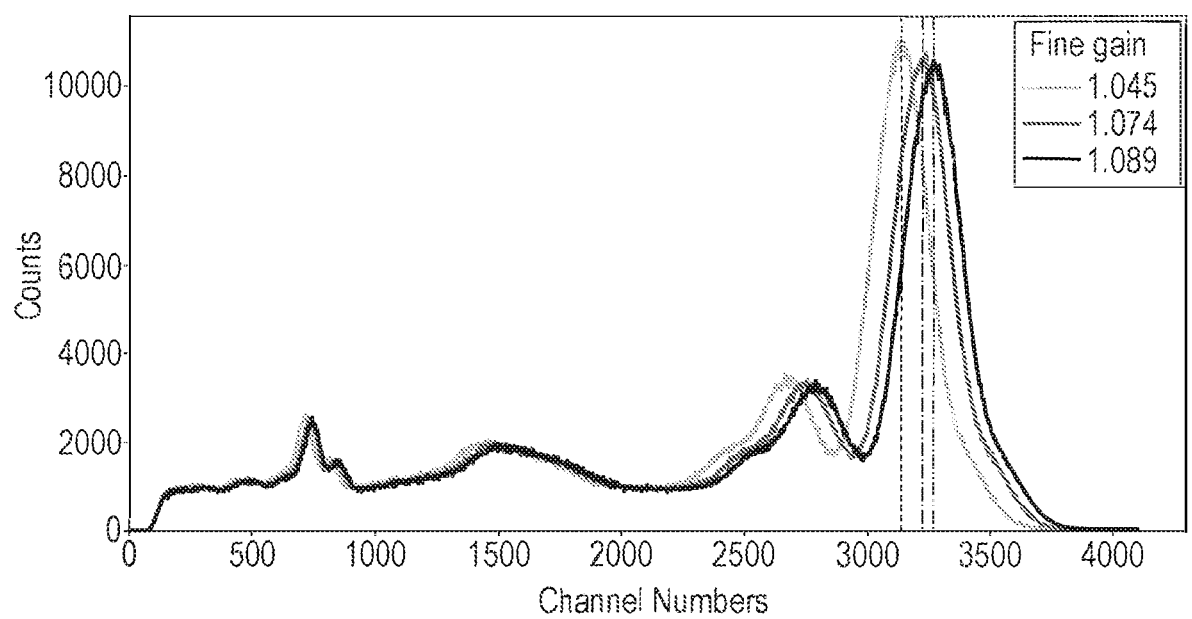
FIG. 18 shows examples of the 356 keV emission line of Ba-133 after is passes through the source's lead shield to the scintillator detector as a function of channel mapping for different values of the digital fine gain.

The two breakthrough gamma plots of FIGS. 11 and 18 are very similar since the lead shields completely stop the Am-241 emission gamma radiation.

Figure 13:
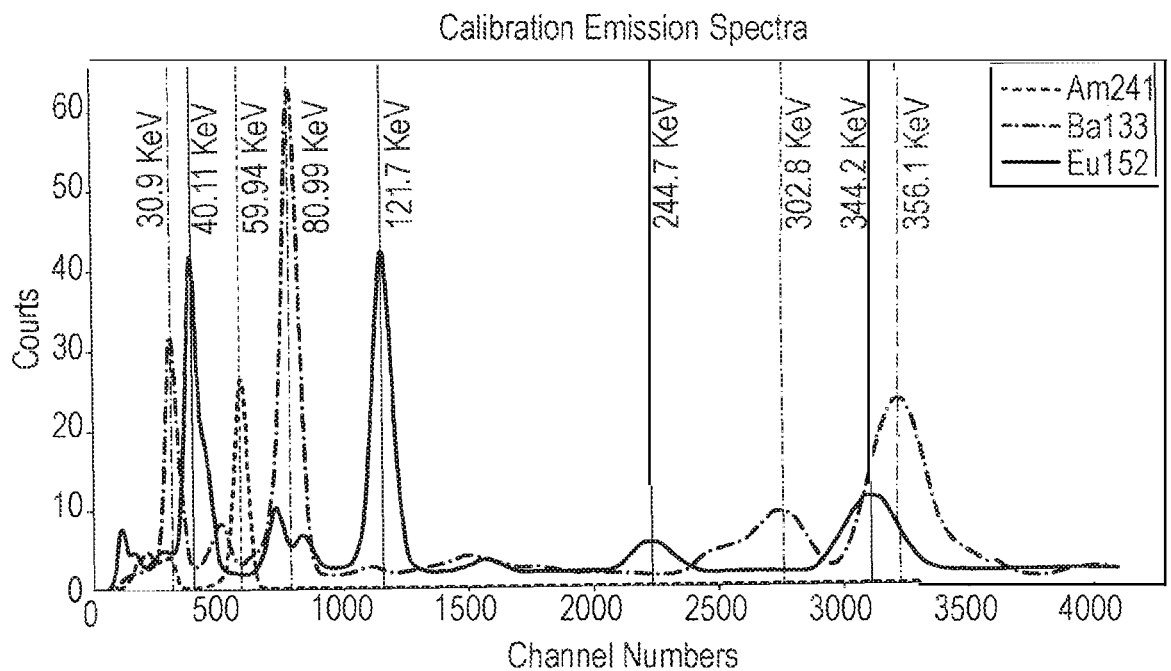
FIG. 13 shows emission spectra for Am-241, Ba-133 and Eu-152 as a function of channel number with energy represented by channel numbers with values ranging from 0 to 4000.

FIG. 13 shows emission spectra for Am-241, Ba-133 and Eu-152 as a function of channel number. The plot contains an apparent typo where the 356 keV gamma line of Ba-133 has been given the value 356.1 keV. This actually is the energy of the line deduced from the channel number to energy mapping function. A 0.1 keV error is actually quite small given that the measured FWHM linewidth of the 356 keV line using our scintillator was about 6.7% (i.e. equivalent to 23.8 keV).

Figure 14:
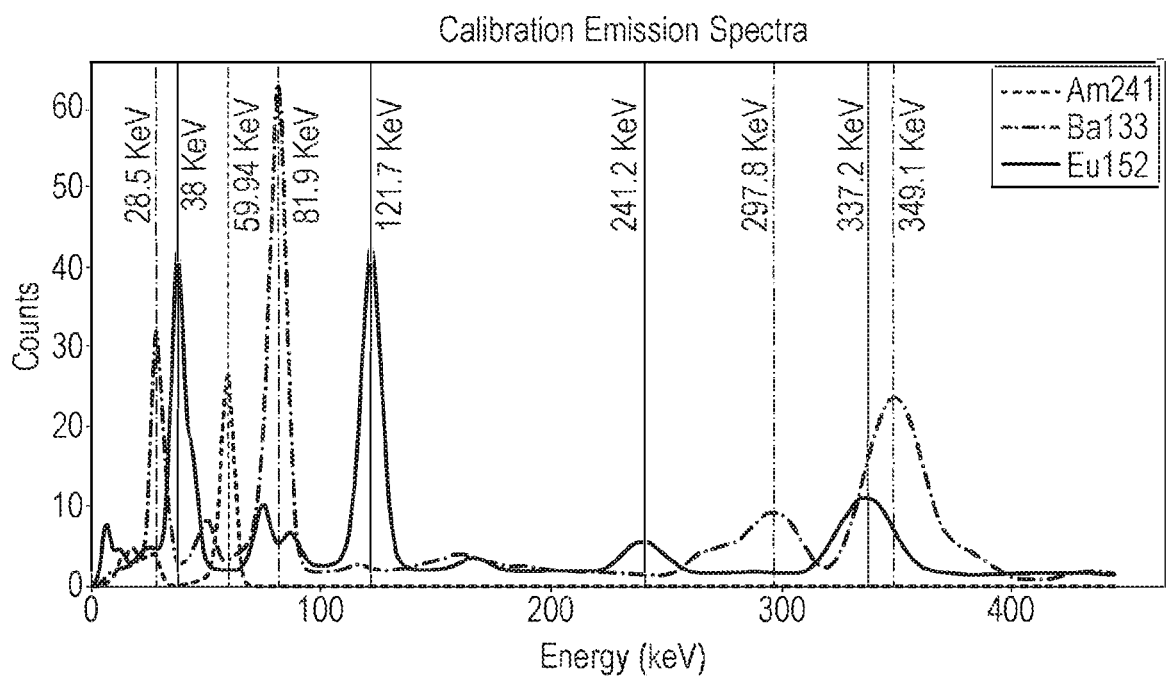
FIG. 14 shows emission spectra for Am-241, Ba-133 and Eu-152 as a function of energy mapping with energy represented in keV with values ranging from 0 to 400.

FIG. 14 shows the emission spectra for Am-241, Ba-133 and Eu-152 as a function of the energy mapping. The values cited on the vertical lines are the energy values for the centroid of the emission lines derived from the energy calibration.

Figure 15:
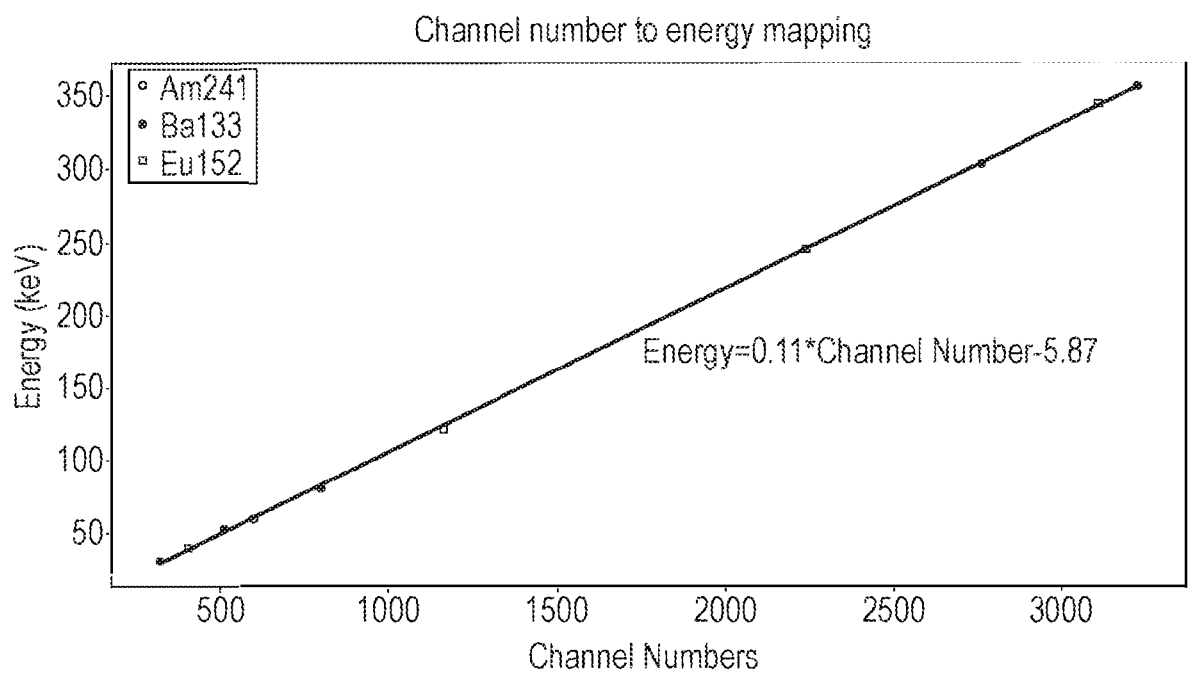
FIG. 15 shows a calibration curve of the channel number to energy mapping.

FIG. 15 shows a calibration curve of channel number to energy mapping. This shows the Fine Gain versus scintillator temperature plot that used in the captured spectra, but with period changes to the Fine Gain value using the Am-241 calibration source (the gold dots). All data were recorded on a single day. The linear fit is given by Energy (keV)=0.11×Channel Number−5.87.

Figure 16:
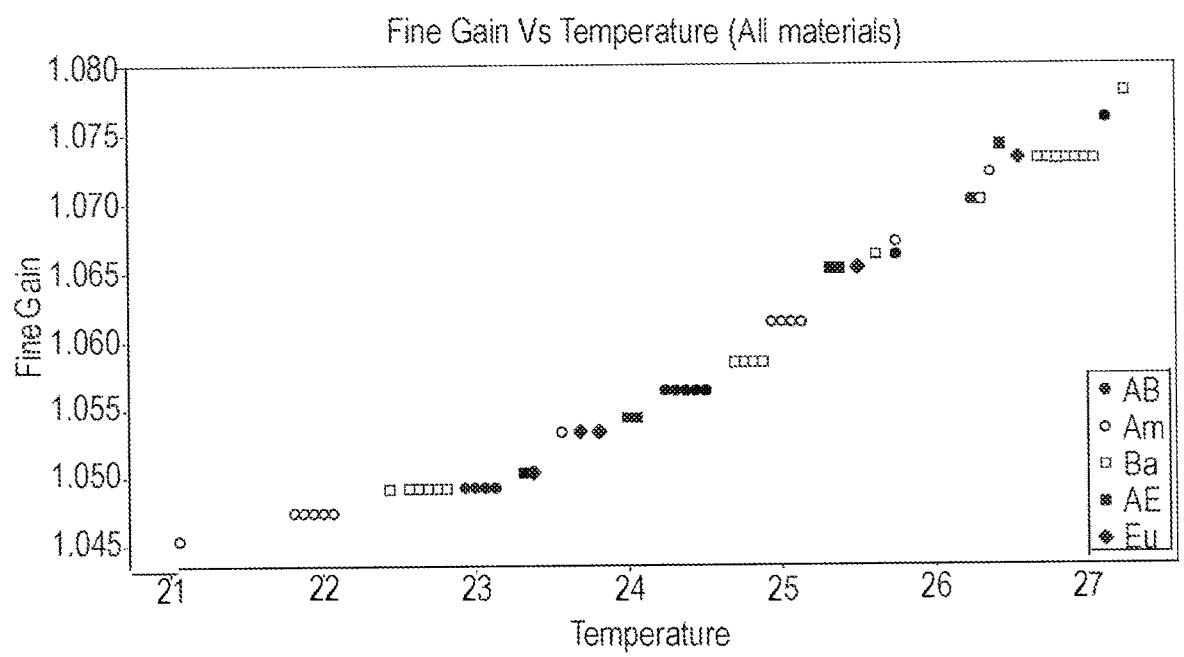
FIG. 16 shows an example curve of digital fine gain as a function of temperature captured on a single day required to maintain the energy calibration of 59.54 keV emission line of Am-241.

FIG. 16 shows a curve of fine gain as a function of temperature for one set of measurements performed on one day (i.e. within 24 hours).

Particularly, FIG. 16 shows an example of drift in digital fine gain required to compensate for temperature induced changes in the scintillator detector energy calibration for the Am-241 calibration measurement obtained during a set of experiments. Fine gain was periodically adjusted to hold the Am-241 emission line of 59.54 keV on Channel 595.4. Colour-coded points in FIG. 14 are shown for: Am-241 (orange); Ba-133 (green); Eu-152 (pink); Am-241 and Ba-133 (blue); and Am-241 and Eu-152 (red).

More specifically, FIG. 16 shows the fine gain values used during the one day of measurements when the temperature of the building varied considerably over the day as the temperature of the room warmed off (room heating was normally switched off and so the room was cold in the morning). However, the relationship between the fine gain and temperature that was required to maintain accurate energy calibration at 59.54 keV was found to vary over longer timescales (i.e. days/weeks) due to changes in the detector's electrical circuit which show a progressive change over time.

Figure 17:
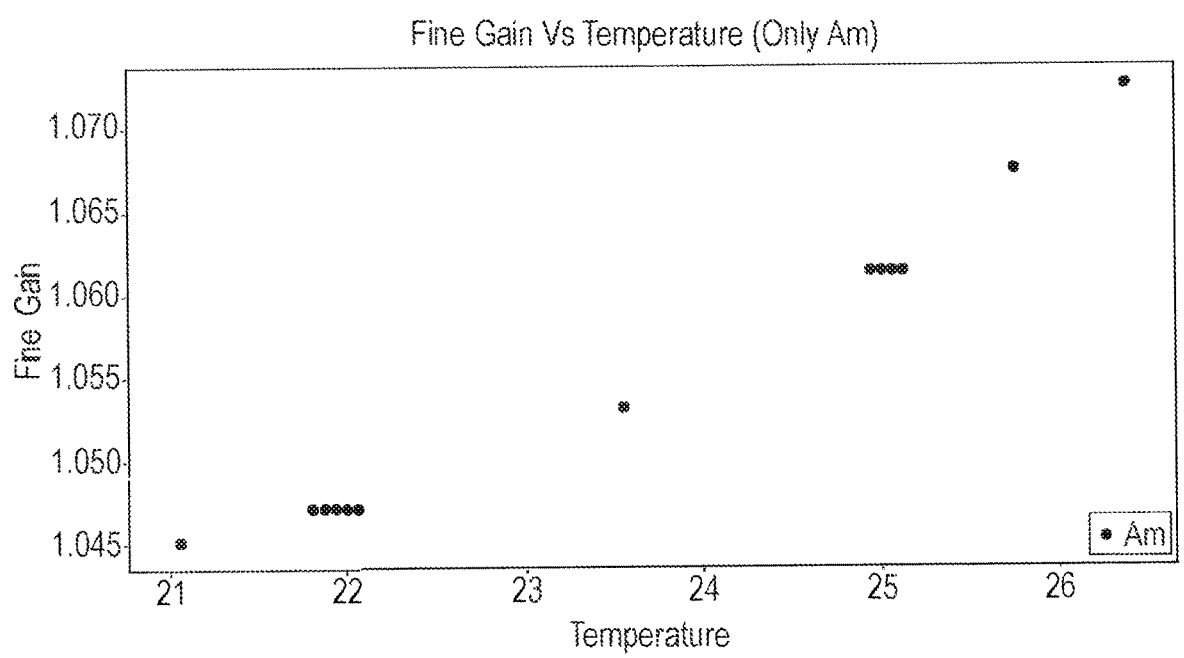
FIG. 17 shows a curve of the digital fine gain as a function of temperature captured on a single day that was required to maintain the energy calibration of 59.54 keV emission line of Am-241.

FIG. 17 shows a calibration curve of fine gain as a function of temperature.

Particularly, FIG. 17 shows an example of drift in digital fine gain required to compensate for temperature induced changes in the scintillator detector energy calibration for the Am-241 Calibration measurement obtained during the set of experiments, as described with respect to FIG. 12. Fine gain was periodically adjusted to hold the Am-241 emission line of 59.54 keV on Channel 595.4. Colour-coded points are shown for: Am-241 (blue) in FIG. 17 (as shown also in FIG. 16 by orange colour-coded points). The calibrated values are the left most blue dot for any given Fine Gain Value. Subsequent dots to the right of the left most dot show how the temperature has changed since the updated calibration was performed. During the experiment, Am-241 spectra were periodically captured to keep track of whether the energy calibration had changed significantly between capturing spectra of explosive samples This data of FIG. 17 are a subset of the data in FIG. 16 and shows only the Fine Gain used for the Am-241 spectra. Note the energy calibration was only ever performed with a single Am-241 source. The left most blue dot corresponds to the new Fine Gain value chosen following a new recalibration. The scintillator temperature then continued to increase, hence two sets of dots forming two separate short lines. The relationship between temperature and the Fine Gain value is not linear.

FIG. 16 and FIG. 17 (i.e. temperature drift) show plots of the measured temperature of the scintillator versus the digital fine gain value set to keep the 59.54 keV line set on energy channel 595.4. The two plots show clearly a monotonic functional connection between the two parameters temperature and the required digital fine gain value needed to maintain the energy calibration. However data captured on different days did not display this direct mapping between the two parameter of temperature and Fine Gain showing that other energy calibration drift effects were also taking place.

There is a risk that the Channel energy mapping may exhibit a gradient for the straight line fit that drifts over time due to various scintillator or electronic circuit drift effects. However by monitoring for example the breakthrough signal at 356 keV and comparing it with a further line at say 59.54 keV due to Am-241, it would be possible to keep track of any such drift in broad energy calibration due to the drift in the electronics or the scintillator or due to radiation dose. Such an Am-241 source would need to be fitted with a mechanical lead shutter of thickness say 2.5 mm or 1.5 mm, as described previously, to virtually totally absorb the gamma emission of Am-241 when backscatter spectra are needed to be captured. Am-241 only significant gamma emission is 59.54 keV gamma and lower energy gamma, all of which are stopped easily with a thin layer of lead. The lead shutter could alternatively be a rotating lead disc with a small aperture which allows calibration spectra and desired backscatter spectra to be captured in parallel through a time division multiplex approach.

FIG. 18 shows examples of the 356 keV emission line of Ba-133 as a function of channel mapping for different values of fine gain.

Particularly, FIG. 18 shows plots of the Am-241 (12 off) plus Ba-133 (7 off) source array breakthrough spectra versus channel number plots for our explosives detection system. These are plotted for three different digital fine gain values that are used to indicate the impact of drifts in the scintillator detect temperature, or other drift effects as discussed below.

In contrast to conventional techniques, the use of 1 or 2 widely spaced Gamma emission lines to correct for drifts due to a combination of drifts in the temperature of the scintillator crystal, drifts in the gain of the photomultiplier, or drifts in the absolute accuracy of the charge measurement circuit is arguably beneficial since it represents a 1 one stop correction for all of these effects. It also can compensate for the additional potential uncertainty that the slope of the linear plot of the of the system between absorbed gamma energy and channel number of the peak response in the multi-channel analyser is not correct due to drifts in all of the above. Measuring the temperature of the scintillator, and or measuring the charge released due to flashes from a calibrated LED will not alone correct for this linear slope gradient variation between energy and channel number recorded by the multi-channel analyser.

Figure 19:
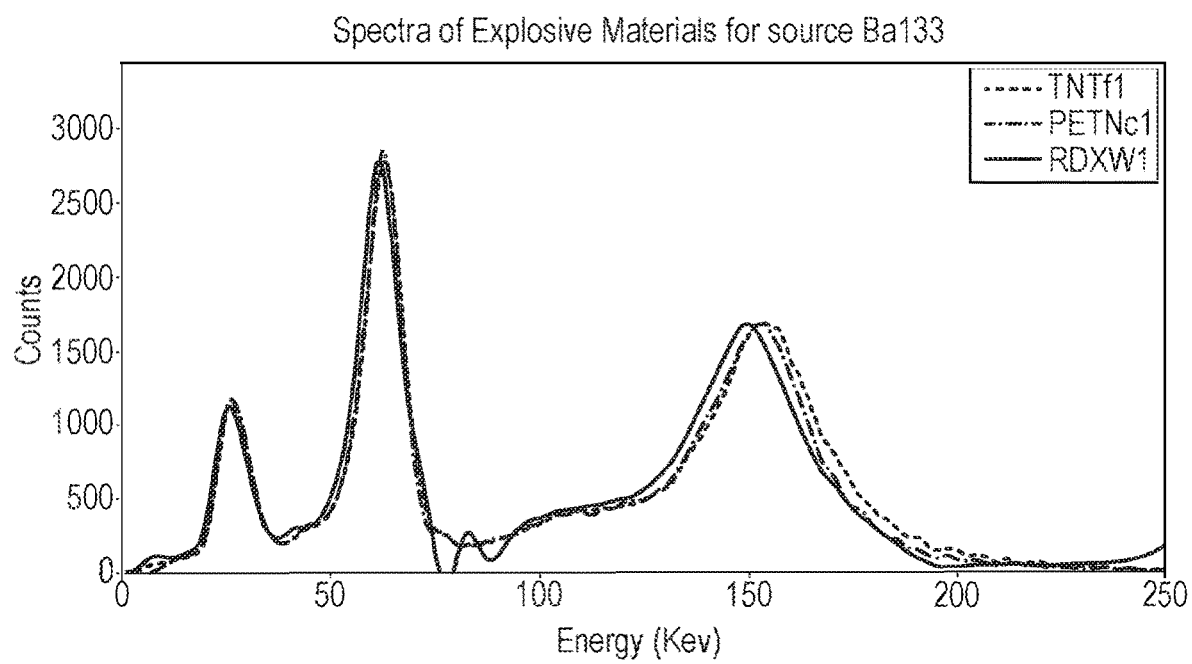
FIG. 19 shows examples of spectra for explosive materials acquired using a source array consisting of solely Ba-133 sources, without gain control according to an exemplary embodiment.

FIG. 19 shows examples of spectra for explosive materials acquired using Ba-133, without gain control according to an exemplary embodiment. The three spectra have been numerically rescaled in amplitude so that the broad peaked feature centred on ~150 keV due principally to backscatter of the 356 keV line of Ba-133 have an approximately identical size for all three spectra. This rescaling allows the observer to note that the three spectra have a virtually identical set of spectral profiles.

Figure 20:
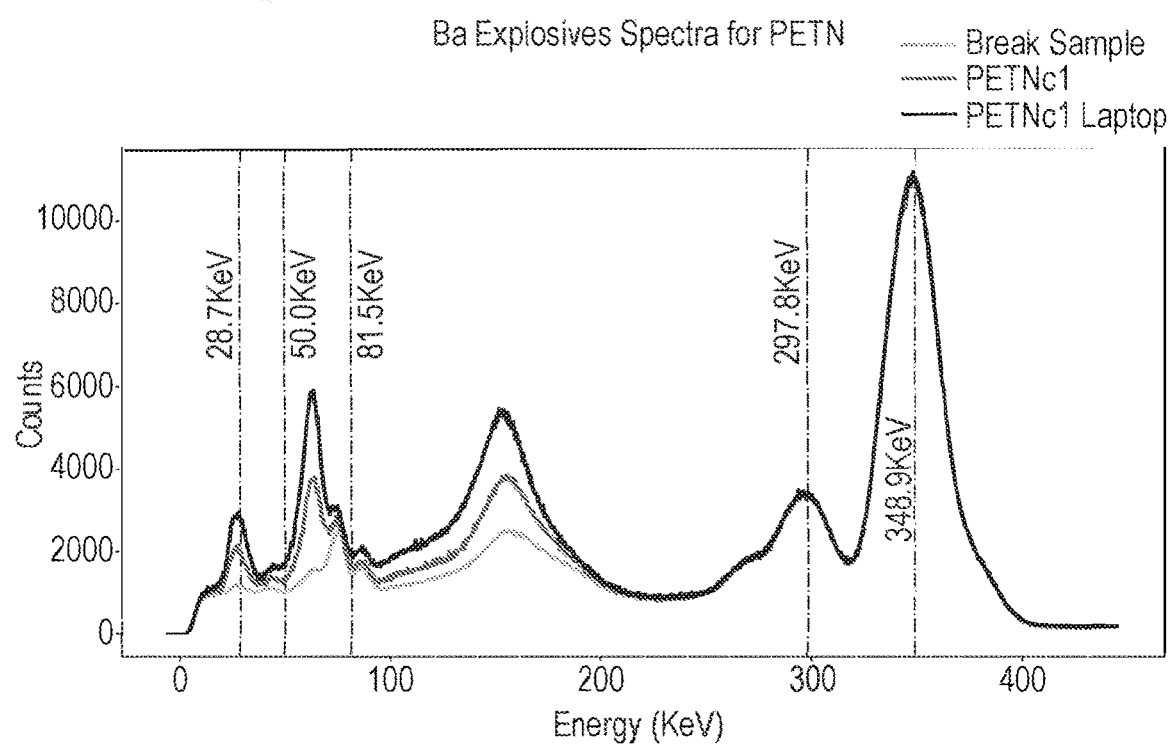
FIG. 20 shows examples of spectra for explosive materials acquired using Ba-133, with gain control according to an exemplary embodiment.

FIG. 20 shows examples of spectra for explosive materials acquired using Ba-133, with gain control according to an exemplary embodiment. The breakthrough and background spectrum has not been subtracted from these spectra. It is to be noted that the large energy peak at measured energy of 348.9 keV is virtually identical for the three spectra comprising: the breakthrough spectrum (blue trace) due to the Ba-133 source array, the measured spectrum of 100 grams of PETN explosive (gold trace), and the measured spectrum for a laptop containing a small 65 gram charge of PETN explosive hidden within the laptop (green trace). Without wishing to be bound by any theory, it is thought it is likely that this similarity of the 348.9 keV peak is due to Compton scattering energy losses: the gamma line generated by the 356 keV line after passing through the Lead shield is likely to be shifted to a lower energy (in this case it was measured to be 348.9 keV). This shift for a given lead shield configuration will however be reliably fixed in value and would not change with time or temperature or indeed any other effects. It therefore can be used as the basis of an energy calibration.

The data in FIG. 18 are a set of gamma spectra captured as the scintillator detector warms up, and demonstrate the drift in the gamma emission line channel number peak. This patent application is targeted at dealing with for example this issue, as well as the additional sources of drift such as drift in the electrical gain of the photomultiplier, and/or its charge sampling circuitry, or changes in the luminescence efficiency of the scintillator due to radiation dose effects. The plots show the impact of variations on the peak position of the 356 keV line, after it has been partly transmitted through the lead shield with some of the incident 356 keV gamma photons suffering from some forward Compton scattering losses on route, due to changes in the gain of the system, both due to either optical luminescence and/or electrical gain.

FIG. 18 shows how the peak due to the 356 keV emission line of Ba-133 drifts for different values of the digital Fine Gain value that were required on different days to achieve an accurate mapping of the 59.54 keV emission line of Am-241 onto Channel 595.4 of the multichannel analyser. The COTS scintillator used for these measurements was a Saint Gobain type SGC-3M3/3 NaI(Tl) Scintillator Detector and Photomultiplier tube. It was operated with a High Voltage of 960 Volts across its dynode chain as this allowed all gammas up to ~400 keV to be displayed across its ~4071 discreet energy channels.

Three vertical lines are in the plot:
  The blue dashed line (left line in FIG. 18) is centred on the peak of the blue trace with a corresponding digital Fine Gain Value of 1.045 to achieve an energy calibrated response for the Am-241 emission line when the temperature of the scintillator crystal was ~23.6° C. The scintillator detector had only just been switched on about 20 minutes earlier and was not yet fully up to it stable operating temperature of ~27° C. for the system located in a clean room with an ambient temperature of 21.3° C. at the time of measurement.

The vertical blue line indicating the peak response passes through Channel ~3140. The reported system temperature of the scintillator crystal when this blue trace was captured was ~27° C. The increased temperature has resulted in a displacement to the left of the peaks position in units of channel numbers.

The green dash line (middle line in FIG. 18) is centred on the peak of the green trace with a corresponding digital Fine Gain Value of 1.074. This was the value needed to achieve an energy calibrated response for the Am-241 emission line when the temperature of the scintillator crystal was now a stable 27° C. having been left on all night to keep it at close to its stable operating temperature.

The vertical green indicating the peak response passes through Channel ~3225. To reiterate the reported system temperature of the scintillator crystal when this green trace was captured was ~27° C., and the peak is now located in approximately the correct position in terms of channel number of the peak response.

The orange dash line (right line in FIG. 18) is centred on the peak response of the orange trace with a corresponding digital Fine Gain Value of 1.089. This fine gain value had been used during earlier work where the scintillator had been at a higher stable temperature of 29° C.

The vertical orange line indicating the peak response passes through Channel ~3270.

The reported system temperature of the scintillator crystal when this orange trace was captured was ~27° C. Again a displacement in the peak's position in units of channel numbers is reported, this time to the right.

The time integration used in these 3 plots was 300 seconds to reduce the impact of shot noise in the individual channels (i.e. root n over n noise).

For a detection system, we compensate for the combined (signal breakthrough and signal background spectra) that are illustrated in these traces by subtracting them from the Compton Backscatter spectra due to the target item under examination. Provided all the traces are correctly calibrated, the resulting corrected spectra will be accurate. However it may be seen how for example subtracting for example the Orange trace from the Blue trace would result in a very large negative count spectrum at channels above 3300. So it is desirable to ensure that an energy calibration is maintained.

Another point to note is that the breakthrough signal recorded when no target specimen is in front of the system accurate monitor for the systems signal response in terms of absolute amplitude since no backscatter signal at 356 keV will exist for our source array consisting of Am-241 sources and Ba-133 sources. Ignoring the progressive reduction in the source activity of the Ba-133 sources over their 10.51 year half-life, this break-through signal should be approximately constant from day to day. This means that one could maintain a library of low shot noise long integration time reference breakthrough spectra on the systems files and by rescaling them to ensure that the peak of the 356 keV line in counts per second is correct, use these to subtract away the unwanted breakthrough signal to reveal the desired true Compton Backscatter spectrum. This opens the possibility to keep a library of such traces for different scintillator detector operating temperatures to avoid having to record in the operational environment a long duration breakthrough signal, or wait a long time for the temperature of the scintillator to become fully stable.

In contrast, FIG. 20 shows an example of the backscatter and breakthrough spectra, where good energy calibration has been constantly maintained. The 356 keV emission line that passed through the lead shield is extremely well aligned in all the plots, and all of the profiles of this emission line are almost perfectly overlaying as one would desire.

Particularly, FIG. 20 shows backscatter plus Breakthrough Spectra superimposed on the Breakthrough Spectra alone. The peak feature at ~70 keV in the Breakthrough spectra combined with differential temperature drift in the energy calibration can give rise to the anomalous oscillation reported at ~80 keV on the RDX/Wax explosive spectra of the explosives slide.

Figure 21:
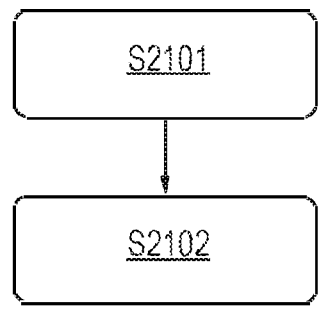
FIG. 21 shows schematically a method according to an exemplary embodiment.

FIG. 21 shows schematically a method according to an exemplary embodiment. Particularly, the method is of controlling a scintillation detector assembly comprising a first scintillation detector of a set of scintillation detectors, comprising a first scintillator of a set of scintillators and a first light sensor of a set of respective light sensors optically coupled thereto, arranged to detect electromagnetic radiation.

At S2101, the first scintillation detector detects first gamma radiation of a first set of gamma radiation, having a first reference energy of a set of first respective reference energies.

At S2102, a gain of the first scintillation detector is controlled based, at least in part, on the first gamma radiation, having the first reference energy, detected by the first scintillation detector.

Optionally, the method comprises at most partially shielding the first scintillation detector from the first gamma radiation.

Optionally, the method comprises alternately at least partially shielding the first scintillation detector from the first gamma radiation and exposing the first scintillation detector from the first gamma radiation.

Figure 22:
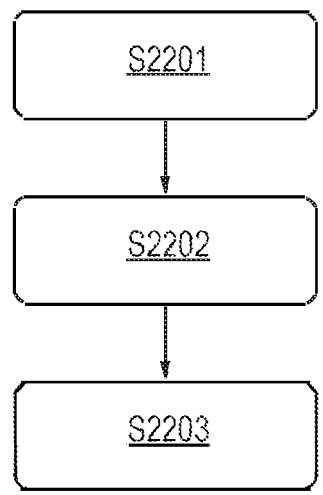
FIG. 22 shows schematically a method according to an exemplary embodiment.

FIG. 22 shows schematically a method according to an exemplary embodiment. Particularly, the method is of determining a calibration for a spectrum, for example a Compton backscatter spectrum.

At S2201, the first scintillation detector detects first gamma radiation of a first set of gamma radiation, having a first reference energy of a set of first respective reference energies.

At S2202, a gain of the first scintillation detector is controlled based, at least in part, on the first gamma radiation, having the first reference energy, detected by the first scintillation detector.

At S2203, the calibration for the spectrum, for example a Compton backscatter spectrum, is determined using the first gamma radiation of the first set of gamma radiation, having the first reference energy of the first set of respective reference energies, detected by the first scintillation detector and optionally, using first gamma radiation of a second set of gamma radiation, having a first reference energy of a second set of respective reference energies, detected by the first scintillation detector.

For example, the calibration may be determined using the 59.54 keV line of Am-241, for example which is used to illuminate the scintillator when a lead shutter is opened, and/or the 356.017 keV line of Ba-133, for example which breaks through a lead shield a least partially shielding the first scintillator detector, for example from a first source. There may be a fixed constant shift in the peak energy of this breakthrough line to a value less than 356 keV due to the impact of Compton scattering losses which at low angles of deflection only yield a small energy shift. However since this will be a fixed effect, the peak of this breakthrough line can still be used as an energy calibrator.

Advantageously, the use of two or more gamma emission lines allows the variation in the scintillator's optical luminescence due to temperature or other effects, together with the separate drifts in the gain of the optical photomultiplier (or other optical detector), or separately drifts in the charge pulse measurement system, to be all calibrated out together.

Optionally, the method comprises at most partially shielding the first scintillation detector from the first gamma radiation.

Optionally, the method comprises alternately at least partially shielding the first scintillation detector from the first gamma radiation and exposing the first scintillation detector from the first gamma radiation.

Figure 23:
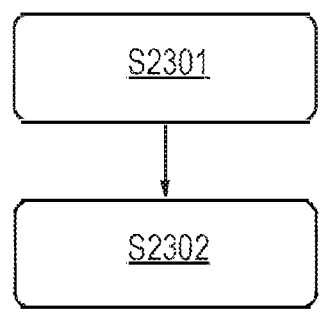
FIG. 23 shows schematically a method according to an exemplary embodiment.

FIG. 23 shows schematically a method according to an exemplary embodiment.

Particularly, the method is of detecting a target using a scintillation detector assembly. The scintillation detector assembly is controlled according to the methods as described with respect to FIG. 17 and/or FIG. 18.

At S2301, a background Compton backscatter spectrum is acquired and a Compton backscatter spectrum of the target is acquired.

At S2302, the Compton backscatter spectrum of the target is background-subtracted using the background Compton backscatter spectrum.

Although a preferred embodiment has been shown and described, it will be appreciated by those skilled in the art that various changes and modifications might be made without departing from the scope of the invention, as defined in the appended claims and as described above.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. A scintillation detector assembly comprising:
    a first scintillation detector of a set of scintillation detectors, the first scintillation detector including a first scintillator of a set of scintillators and a first light sensor of a set of respective light sensors optically coupled thereto, arranged to detect electromagnetic radiation and output a first signal;
    a first radiation source of a set of radiation sources, configured to emit first gamma radiation of a first set of gamma radiation, having a first reference energy of a set of respective first reference energies;
    a first radiation shutter of a set of radiation shutters, the first radiation shutter movable between a first configuration to at least partially shield the first scintillation detector from the first radiation source and a second configuration to selectively expose the first scintillation detector to the first radiation source, the movement of the first radiation shutter for generating a pulse of the first radiation at the first scintillation detector; and
    a controller configured to control a gain of the first scintillation detector based, at least in part, on the first gamma radiation, having the first reference energy, and a first detected energy detected by the first scintillation detector in response to exposure to the pulse of the first gamma radiation, wherein the first detected energy is different from the first reference energy, the controller further configured to control the gain of the first scintillation detector by causing the first radiation shutter to move between the first and second configurations.

2. The scintillation detector assembly according to claim 1, comprising a first radiation shield of a set of radiation shields, arranged to at most partially shield the first scintillation detector from the first radiation source.

3. The scintillation detector assembly according to claim 1, wherein the first radiation source is configured to emit second gamma radiation of the first set of gamma radiation, having a second reference energy of the set of respective first reference energies; wherein the controller is configured to control the gain of the first scintillation detector based, at least in part, on the second gamma radiation of the first set of gamma radiation, having the second reference energy of the set of respective first reference energies, and a second detected energy detected by the first scintillation detector in response to exposure to the second gamma radiation, and wherein the second detected energy is different from the second reference energy.

4. The scintillation detector assembly according to claim 1, comprising a second radiation source of the set of radiation sources, configured to emit first gamma radiation of a second set of gamma radiation, having a first reference energy of a set of respective second reference energies; wherein the controller is configured to control the gain of the first scintillation detector based, at least in part, on the first gamma radiation of the second set of gamma radiation, having the first reference energy of the set of respective second reference energies, and a second detected energy detected by the first scintillation detector in response to exposure to the first gamma radiation of the second set of gamma radiation, and wherein the second detected energy is different from the first reference energy of the set of respective second reference energies.

5. The scintillation detector assembly according to claim 1, wherein the controller is configured to control the gain of the first scintillation detector according to a temperature change of the first scintillator, a gain change of the first light sensor and/or an accuracy change of the first signal.

6. The scintillation detector assembly according to claim 1, wherein the first radiation source comprises Ba-133, Am-241 and/or Eu-152.

7. The scintillation detector assembly according to claim 1, wherein the first scintillator comprises an inorganic crystal.

8. The scintillation detector assembly according to claim 7, wherein the first scintillator comprises NaI(Tl) (thallium-doped sodium iodide), CsI(Tl), CsI(Na), CsI(pure), CsF, KI(Tl), LiI(Eu), BaF2, CaF2(Eu), ZnS(Ag), CaWO4, CdWO4, YAG(Ce) (Y3Al5O12(Ce)), GSO, LSO, LaCl3 (Ce), LaBr3(Ce), LYSO (Lu0.8Y0.2SiO5(Ce)) and/or BGO.

9. The scintillation detector assembly according to claim 1, wherein the first light sensor comprises a photomultiplier tube (PMT), photodiode, or silicon photomultiplier.

10. The scintillation detector assembly according to claim 9, wherein the first light sensor comprises an avalanche photodiode or a single photon avalanche photodiode.

11. A Compton radiation backscatter detector comprising a scintillation detector assembly according to claim 1.

12. A method of controlling a scintillation detector assembly, the assembly including a first scintillation detector of a set of scintillation detectors, the first scintillation detector including a first scintillator of a set of scintillators and a first light sensor of a set of respective light sensors optically coupled thereto, arranged to detect electromagnetic radiation, the assembly further comprising a first radiation shutter of a set of radiation shutters, the first radiation shutter movable between a first configuration to at least partially shield the first scintillation detector from the first radiation source and a second configuration to selectively expose the first scintillation detector to the first radiation source, the movement of the first radiation shutter for generating a pulse of the first radiation at the first scintillation detector, the method comprising:
  detecting, by the first scintillation detector, first detected energy in response to exposure of the pulse of the first scintillation detector to first gamma radiation of a first set of gamma radiation, having a first reference energy of a set of first respective reference energies; and
  controlling a gain of the first scintillation detector based, at least in part, on the first gamma radiation, having the first reference energy, and the first detected energy detected by the first scintillation detector by causing the first radiation shutter to move between the first and second configurations, wherein the first detected energy is different from the first reference energy.

13. The method according to claim 12, comprising at most partially shielding the first scintillation detector from the first gamma radiation.

14. The method according to claim 12, comprising:
  at least partially shielding the first scintillation detector from the first gamma radiation; and
  exposing the first scintillation detector to the first gamma radiation.

15. The method according to claim 12, comprising:
  determining a calibration for a spectrum, using the first gamma radiation of the first set of gamma radiation, having the first reference energy of the first set of respective reference energies, detected by the first scintillation detector.

16. The method according to claim 15, wherein the spectrum is a Compton backscatter spectrum.

17. The method according to claim 15, wherein determining the calibration for the spectrum including using first gamma radiation of a second set of gamma radiation, having a first reference energy of a second set of respective reference energies, detected by the first scintillation detector.

18. A method of detecting a target using a scintillation detector assembly, the method comprising:
  acquiring a background Compton backscatter spectrum and a Compton backscatter spectrum of the target; and
  background-subtracting the Compton backscatter spectrum of the target using the background Compton backscatter spectrum;
  wherein the scintillation detector assembly is controlled according to the method of claim 12.

\* \* \* \* \*